(12) United States Patent
Ito et al.

(10) Patent No.: US 8,729,093 B2
(45) Date of Patent: *May 20, 2014

(54) SOIL TREATING AGENT OR SEED TREATING AGENT COMPRISING QUINOLINE COMPOUNDS OR SALTS THEREOF AS ACTIVE INGREDIENT, OR METHOD FOR PREVENTING PLANT DISEASES BY USING THE SAME

(75) Inventors: Hiroyuki Ito, Shiga (JP); Yasushi Tamagawa, Shiga (JP); Harukazu Tanaka, Shiga (JP); Toshiaki Ohara, Shiga (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 16 days.

This patent is subject to a terminal disclaimer.

(21) Appl. No.: 12/312,896

(22) PCT Filed: Nov. 30, 2007

(86) PCT No.: PCT/JP2007/073143
§ 371 (c)(1),
(2), (4) Date: May 29, 2009

(87) PCT Pub. No.: WO2008/066148
PCT Pub. Date: Jun. 5, 2008

(65) Prior Publication Data
US 2009/0325998 A1    Dec. 31, 2009

(30) Foreign Application Priority Data
Dec. 1, 2006    (JP) ................... 2006-325344

(51) Int. Cl.
*A01N 43/42*    (2006.01)
*A01P 15/00*    (2006.01)

(52) U.S. Cl.
USPC .......................................... 514/291; 514/314

(58) Field of Classification Search
None
See application file for complete search history.

(56) References Cited

U.S. PATENT DOCUMENTS

| | | | | |
|---|---|---|---|---|
| 5,169,855 | A * | 12/1992 | Cain et al. ............ | 514/319 |
| 7,122,672 | B2 * | 10/2006 | Salmon et al. ........ | 546/141 |
| 7,632,783 | B2 * | 12/2009 | Ito et al. ............... | 504/247 |
| 2007/0032490 | A1 * | 2/2007 | Ackermann et al. ... | 514/235.5 |
| 2008/0275242 | A1 | 11/2008 | Ito et al. | |

FOREIGN PATENT DOCUMENTS

| | | |
|---|---|---|
| EP | 1 736 471 A1 | 12/2006 |
| JP | 46-5099 A | 11/1971 |
| JP | 2005-232081 * | 9/2005 |
| WO | WO2005/070917 * | 8/2005 |
| WO | WO 2007/011022 A1 | 1/2007 |

OTHER PUBLICATIONS

Machine Translation of WO/2005/070917.*
Machine Translation of JP 2005-232081.*

(Continued)

*Primary Examiner* — Mina Haghighatian
*Assistant Examiner* — Erin Hirt
(74) *Attorney, Agent, or Firm* — Holtz Holtz Goodman & Chick, P.C.

(57) ABSTRACT

A soil treating agent or a seed treating agent having excellent prevention effects against various plant pathogens (particularly against rice blast) is provided.
A soil treating agent or seed treating agent, comprising one or more compounds of the general formula (Ia), (Ib) or (Ic):

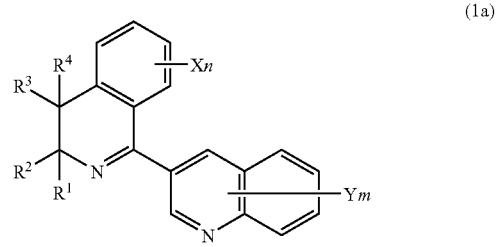

(Ia)

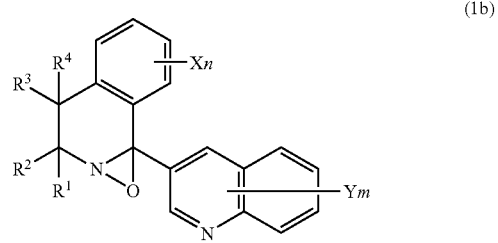

(Ib)

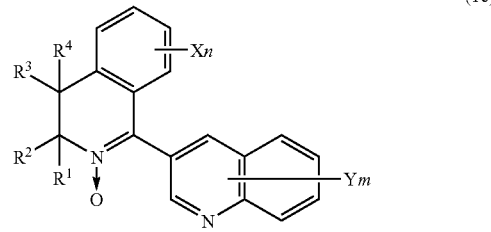

(Ic)

(wherein $R^1$, $R^2$: $C_1$-$C_6$ alkyl (may be substituted), aryl (may be substituted), heteroaryl (may be substituted), aralkyl (may be substituted) and the like; $R^3$, $R^4$: H, $C_1$-$C_6$ alkyl (may be substituted), halogen, $C_1$-$C_6$ alkoxy and the like; X: halogen, $C_1$-$C_6$ alkyl (may be substituted), $C_2$-$C_6$ alkenyl (may be substituted), $C_2$-$C_6$ alkynyl (may be substituted), aryl (may be substituted), heteroaryl (may be substituted), $C_1$-$C_6$ alkoxy and the like; Y: halogen, $C_1$-$C_6$ alkyl, $C_1$-$C_6$ alkoxy, OH; n: 0 to 4; m: 0 to 6)
or salts thereof as an active ingredient.

7 Claims, No Drawings

(56) References Cited

OTHER PUBLICATIONS

McGee D.C., "Advances in Seed Treatment Technology", Asian Seed Conference, New Delhi, India, Sep. 27-29, 1995 (17 pages).
Extended European Search Report dated Dec. 14, 2010 in the corresponding EP application EP 07 83 2840 (6 pages).
U.S. Appl. No. 10/587,100, filed Jul. 21, 2006.
Japanese Office Action dispatched on Feb. 26, 2013, which issued in the counterpart Japanese Patent Application No. 2008-547048, and an English-language translation thereof.

* cited by examiner

SOIL TREATING AGENT OR SEED TREATING AGENT COMPRISING QUINOLINE COMPOUNDS OR SALTS THEREOF AS ACTIVE INGREDIENT, OR METHOD FOR PREVENTING PLANT DISEASES BY USING THE SAME This application is the United States national phase application of International Application PCT/JP2007/073143 filed Nov. 30, 2007.

TECHNICAL FIELD

The present invention relates to a soil treating agent (a composition for preventing plant diseases characterized in treating soil) or to a seed treating agent (a composition for preventing plant diseases characterized in treating seeds), comprising one or more 3-(dihydroisoquinolin-1-yl)quinoline compounds or salts thereof as an active ingredient.

In addition, the present invention relates to a method for preventing plant diseases by using a soil treating agent (a composition for preventing plant diseases characterized in treating soil) or by using a seed treating agent (a composition for preventing plant diseases characterized in treating seeds), comprising one or more 3-(dihydroisoquinolin-1-yl)quinoline compounds or salts thereof as an active ingredient.

BACKGROUND ART 3-(Dihydroisoquinolin-1-yl)quinoline compounds are publicly known compounds, and are known to be useful for an agricultural and horticultural fungicide (Patent Document 1). This document particularly explains clearly the fungicidal effect against rice blast (*Pyricularia oryzae*) and tomato gray mold (*Botrytis cinerea*).

However, this document does not describe a fungicidal effect against rice blast by treating soil in a nursery box for growing young plants during the period of sowing time to transplanting time, and it has not been known that 3-(dihydroisoquinolin-1-yl)quinoline compounds have a fungicidal effect against rice blast by treating soil.

In addition, this document does not describe that 3-(dihydroisoquinolin-1-yl)quinoline compounds have a fungicidal effect against soil diseases by soil-drenching treatment and it has not been known that 3-(dihydroisoquinolin-1-yl)quinoline compounds can be used as a preventing agent against soil diseases.

Further, this document does not describe use of 3-(dihydroisoquinolin-1-yl)quinoline compounds as a seed treating agent and it has not been known that 3-(dihydroisoquinolin-1-yl)quinoline compounds can be used as a seed treating agent. Patent Document 1: Pamphlet of International Publication WO 2005/70917

DISCLOSURE OF THE INVENTION

Problems to be Solved by the Invention

As a result of conducting extensive studies on the 3-(dihydroisoquinolin-1-yl)quinoline compounds for many years, the inventors of the present invention newly found that the present compounds are useful as a soil treating agent or as a seed treating agent, thereby leading to completion of the present invention.

The present invention provides a soil treating agent (a composition for preventing plant diseases characterized in treating soil) or a seed treating agent (a composition for preventing plant diseases characterized in treating seeds), comprising one or more 3-(dihydroisoquinolin-1-yl)quinoline compounds or salts thereof as an active ingredient.

In addition, the present invention provides a method for preventing plant diseases by using a soil treating agent (a composition for preventing plant diseases characterized in treating soil) or by using a seed treating agent (a composition for preventing plant diseases characterized in treating seeds), comprising one or more 3-(dihydroisoquinolin-1-yl)quinoline compounds or salts thereof as an active ingredient.

In the present invention, "a preventive effect" means a preventive effect and/or a curative effect.

Means for Solving the Problems

The present invention relates to a soil treating agent or a seed treating agent, comprising one or more compounds of the general formula (Ia), (Ib) or (Ic):

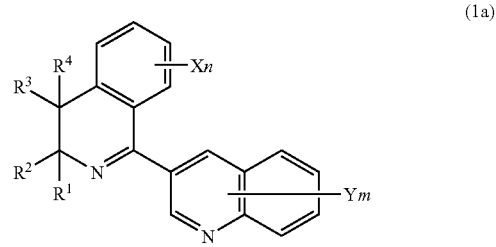

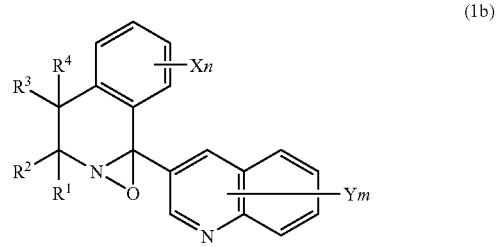

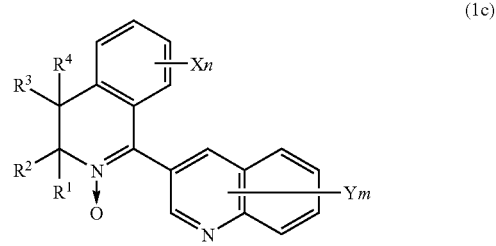

(wherein
$R^1$ and $R^2$ may be the same or different, and represent
a $C_1$-$C_6$ alkyl group which may be substituted with 1 to 3 of the same or different substituents selected from the group consisting of a halogen atom, $C_1$-$C_6$ alkoxy group, $C_1$-$C_6$ alkylthio group and phenoxy group;
an aryl group which may be substituted with 1 to 6 of the same or different substituents selected from the group consisting of a halogen atom, $C_1$-$C_6$ alkyl group which may be substituted with 1 to 3 of the same or different halogen atoms, $C_1$-$C_6$ alkoxy group, amino group which may be substituted with 1 to 2 of the same or different $C_1$-$C_6$ alkyl groups or acyl groups, nitro group, cyano group, hydroxyl group, mercapto group, and $C_1$-$C_6$ alkylthio group;
a heteroaryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group; or an aralkyl group which may be substituted with 1 to 6 of the same or different substituents selected from the group consisting of a halogen atom, $C_1$-$C_6$ alkyl group which may be substituted with 1 to 3 of the same or different halogen atoms, $C_1$-$C_6$ alkoxy group, amino group which may be substituted with 1 to 2 of the same or different $C_1$-$C_6$ alkyl groups or acyl groups, nitro group, cyano group, hydroxyl group, mercapto group and $C_1$-$C_6$ alkylthio group, or $R^1$ and $R^2$ together with the carbon atom to which they are bound, form a $C_3$-$C_{10}$ cycloalkyl ring which may be substituted with 1 to 3 of the same or different substituents selected from the group consisting of a halogen atom, $C_1$-$C_6$ alkyl group, $C_1$-$C_6$ alkoxy group and phenoxy group, $R^3$ and $R^4$ may be the same or different, and represent
 a hydrogen atom;
 a $C_1$-$C_6$ alkyl group which may be substituted with 1 to 3 of the same or different substituents selected from the group consisting of a halogen atom, $C_1$-$C_6$ alkoxy group, $C_1$-$C_6$ alkylthio group and phenoxy group;
 a halogen atom;
 a $C_1$-$C_6$ alkoxy group; or
 a hydroxyl group, or $R^3$ and $R^4$ together form a $C_1$-$C_6$ alkylidene group or oxo group; or together with the carbon atom to which they are bound, form a $C_3$-$C_{10}$ cycloalkyl ring which may be substituted with 1 to 3 of the same or different substituents selected from the group consisting of a halogen atom, $C_1$-$C_6$ alkyl group, $C_1$-$C_6$ alkoxy group and phenoxy group;

X may be the same or different when n is 2 to 4, and represent
 a halogen atom;
 a $C_1$-$C_6$ alkyl group which may be substituted with 1 to 3 of the same or different substituents selected from the group consisting of a halogen atom, $C_1$-$C_6$ alkoxy group, hydroxyl group, $C_2$-$C_7$ alkoxycarbonyl group and phenoxy group;
 a $C_2$-$C_6$ alkenyl group which may be substituted with 1 to 3 of the same or different substituents selected from the group consisting of a halogen atom, $C_1$-$C_6$ alkoxy group, $C_2$-$C_7$ alkoxycarbonyl group and phenoxy group;
 a $C_2$-$C_6$ alkynyl group which may be substituted with 1 to 3 of the same or different substituents selected from the group consisting of a halogen atom, $C_1$-$C_6$ alkoxy group and phenoxy group;
 an aryl group which may be substituted with 1 to 6 of the same or different substituents selected from the group consisting of a halogen atom, $C_1$-$C_6$ alkyl group which may be substituted with 1 to 3 of the same or different halogen atoms, $C_1$-$C_6$ alkoxy group, amino group which may be substituted with 1 to 2 of the same or different $C_1$-$C_6$ alkyl groups or acyl groups, nitro group, cyano group, hydroxyl group, mercapto group and $C_1$-$C_6$ alkylthio group;
 a heteroaryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group;
 a $C_1$-$C_6$ alkoxy group;
 an amino group which may be substituted with 1 to 2 of the same or different $C_1$-$C_6$ alkyl groups or acyl groups;
 an acyl group;
 a cyano group; or
 a N-hydroxyalkanimidoyl group in which a hydrogen atom of the hydroxyl group may be substituted with a substituent selected from the group consisting of a $C_1$-$C_6$ alkyl group, $C_2$-$C_6$ alkenyl group, $C_2$-$C_6$ alkynyl group, aralkyl group, aryl group and heteroaryl group, Y may be the same or different when m is 2 to 6, and represent
 a halogen atom; $C_1$-$C_6$ alkyl group; $C_1$-$C_6$ alkoxy group; or hydroxyl group,
 n represents an integer of 0 to 4, and
 m represents an integer of 0 to 6)
or salts thereof as an active ingredient.

Here, in compounds (Ia), (Ib) and (Ic), X represents a hydrogen atom when n is 0, and Y represents a hydrogen atom when m is 0.

Effects of the Invention 3-(Dihydroisoquinolin-1-yl)quinoline compounds (Ia), (Ib) and (Ic) of the present invention can be used as a soil treating agent or as a seed treating agent, and show outstanding effects against various plant pathogens, particularly against rice blast without causing damage to host plants and have superior preventing effects against plant diseases as a soil treating agent or as a seed treating agent.

BEST MODE FOR CARRYING OUT THE INVENTION

In compounds (Ia), (Ib) and (Ic) of the present invention, "$C_1$-$C_6$ alkyl group" may be a linear or branched alkyl group having 1 to 6 carbon atoms, including for example a methyl group, ethyl group, propyl group, isopropyl group, butyl group, isobutyl group, s-butyl group, t-butyl group, pentyl group, isopentyl group, 2-methyl-butyl group, neopentyl group, 1-ethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group or 2-ethylbutyl group, preferably a linear or branched alkyl group having 1 to 5 carbon atoms ($C_1$-$C_5$ alkyl group), more preferably a linear or branched alkyl group having 1 to 4 carbon atoms ($C_1$-$C_4$ alkyl group), still more preferably a linear or branched alkyl group having 1 to 3 carbon atoms ($C_1$-$C_3$ alkyl group), particularly preferably a methyl group, ethyl group or propyl group and most preferably a methyl group or ethyl group.

In compounds (Ia), (Ib) and (Ic) of the present invention, a "$C_2$-$C_6$ alkenyl group" may be linear or branched and may contain one or an arbitrary number of double bonds, including for example a vinyl group, prop-1-en-1-yl group, allyl group, isopropenyl group, but-1-en-1-yl group, but-2-en-1-yl group, but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group or 4-methylpent-3-en-1-yl group, preferably a vinyl group, allyl group, isopropenyl group or but-1-en-1-yl group and more preferably an allyl group or isopropenyl group.

In compounds (Ia), (Ib) and (Ic) of the present invention, a "$C_2$-$C_6$ alkynyl group" may be linear or branched and may contain one or an arbitrary number of triple bonds, including for example an ethynyl group, prop-1-yn-1-yl group, prop-2-yn -1-yl group, but-1-yn-1-yl group, but-3-yn-1-yl group, 1-methylprop-2-yn-1-yl group, pent-1-yn-1-yl group, pent- 4-yn-1-yl group, hex-1-yn-1-yl group or hex-5-yn-1-yl group and preferably an ethynyl group or prop-1-yn-1-yl group.

In compounds (Ia), (Ib) and (Ic) of the present invention, an "aryl group" may be, for example, an $C_6$-$C_{16}$ aromatic hydrocarbon group (6 to 16 carbons), including for example a phenyl group, 1-naphthyl group, 2-naphthyl group, anthracenyl group, phenanthrenyl group or acenaphthylenyl group, preferably a phenyl group, 1-naphthyl group or 2-naphthyl group and more preferably a phenyl group.

In compounds (Ia), (Ib) and (Ic) of the present invention, a "heteroaryl group" may have a single ring or multiple rings, and may contain one or two or more of the same or different ring-composing heteroatoms, wherein there is no particular limitations on the type of heteroatom, and may be a nitrogen atom, oxygen atom or sulfur atom for example. Heteroaryl group may be, for example, 5- to 7-member monocyclic heteroaryl group, including a furyl group, thienyl group, pyrrolyl group, oxazolyl group, isoxazolyl group, dihydroisoxazolyl group, thiazolyl group, isothiazolyl group, imidazolyl group, pyrazolyl group, oxadiazolyl group, thiadiazolyl group, triazolyl group, tetrazolyl group, pyridyl group, azepinyl group and oxazepinyl group, and polycyclic heteroaryl group which compose a heteroaryl group may be 8- to 14-member polycyclic heteroaryl group, including a benzofuranyl group, isobenzofuranyl group, benzothienyl group, indolyl group, isoindolyl group, indazolyl group, benzoazolyl group, benzisoxazolyl group, benzothiazolyl group, benzisothiazolyl group, benzoxadiazolyl group, benzothiadiazolyl group, benzotriazolyl group, quinolyl group, isoquinolyl group, cinnolinyl group, quinazolinyl group, quinoxalinyl group, phthalazinyl group, naphthyridinyl group, purinyl group, pteridinyl group, carbazolyl group, carbolinyl group, acridinyl group, 2-acridinyl group, 3-acridinyl group, 4-acridinyl group, 9-acridinyl group, phenoxazinyl group, phenothiazinyl group or phenazinyl group, preferably a furyl group, thienyl group, oxazolyl group, pyridyl group, benzofuranyl group or isobenzofuranyl group, more preferably a furyl group, thienyl group, oxazolyl group or pyridyl group, and particularly preferably a furyl group or thienyl group.

In compounds (Ia), (Ib) and (Ic) of the present invention, an "aralkyl group" may be a group in which one, or two or more hydrogen atoms (preferably 1 to 3 hydrogen atoms, more preferably 1 to 2 hydrogen atoms) of the aforementioned "$C_1$-$C_6$ alkyl group" is substituted with the aforementioned "aryl group", including for example a benzyl group, 1-naphthylmethyl group, 2-naphthylmethyl group, anthracenylmethyl group, phenanthrenylmethyl group, acenaphthylenylmethyl group, diphenylmethyl group, 1-phenethyl group, 2-phenethyl group, 1-(1-naphthyl)ethyl group, 1-(2-naphthyl)ethyl group, 2-(1-naphthyl)ethyl group, 2-(2-naphthyl)ethyl group, 3-phenyl-propyl group, 3-(1-naphthyl)propyl group, 3-(2-naphthyl)propyl group, 4-phenylbutyl group, 4-(1-naphthyl)butyl group, 4-(2-naphthyl)butyl group, 5-phenylpentyl group, 5-(1-naphthyl)pentyl group, 5-(2-naphthyl)pentyl group, 6-phenylhexyl group, 6-(1-naphthyl)hexyl group or 6-(2-naphthyl)hexyl group, preferably a benzyl group, diphenylmethyl group, 1-phenethyl group or 2-phenethyl group and more preferably a benzyl group.

In compounds (Ia), (Ib) and (Ic) of the present invention, a "$C_3$-$C_{10}$ cycloalkyl ring" is a cyclic hydrocarbon group which is formed by binding an alkylene group having 2 to 9 carbon atoms, including for example an ethylene group, trimethylene group, tetramethylene group, pentamethylene group, hexamethylene group, heptamethylene group, octamethylene group and the like to one carbon atom, preferably a cyclic hydrocarbon group which is formed by binding a trimethylene group, tetramethylene group or pentamethylene group (cyclobutyl ring, cyclopentyl ring or cyclo-hexyl ring) and more preferably a cyclic hydrocarbon group which is formed by binding a pentamethylene group (cyclohexyl ring).

In compounds (Ia), (Ib) and (Ic) or the present invention, a "halogen atom" is a fluorine atom, chlorine atom, bromine atom or iodine atom, preferably a fluorine atom, chlorine atom or bromine atom, more preferably a fluorine atom or chlorine atom and most preferably a fluorine atom.

In compounds (Ia), (Ib) and (Ic) of the present invention, a "$C_1$-$C_6$ alkoxy group" is a linear or branched alkoxy group having 1 to 6 carbon atoms, including for example a methoxy group, ethoxy group, propoxy group, isopropoxy group, butoxy group, isobutoxy group, s-butoxy group, t-butoxy group, pentyloxy group, isopentyloxy group, 2-methylbutoxy group, neopentyloxy group, 1-ethylpropoxy group, hexyloxy group, (4-methylpentyl)oxy group, (3-methylpentyl)oxy group, (2-methylpentyl)oxy group, (1-methylpentyl)oxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group or 2-ethylbutoxy group, preferably a linear or branched alkoxy group having 1 to 4 carbon atoms ($C_1$-$C_4$ alkoxy group), more preferably a methoxy group, ethoxy group or isopropoxy group, still more preferably a methoxy group or ethoxy group and most preferably a methoxy group.

In compounds (Ia), (Ib) and (Ic) of the present invention, a "$C_1$-$C_6$ alkylthio group" is a linear or branched alkylthio group having 1 to 6 carbon atoms, including for example a methylthio group, ethylthio group, propylthio group, isopropylthio group, butylthio group, isopentylthio group, neopentylthio group, 3,3-dimethylbutylthio group or 2-ethylbutylthio group, preferably a linear or branched alkylthio group having 1 to 4 carbon atoms and more preferably a methylthio group.

In compounds (Ia), (Ib) and (Ic) of the present invention, an "acyl group" may be a formyl group, carbonyl group to which the aforementioned "$C_1$-$C_6$ alkyl group" is bound ($C_2$-$C_7$ alkylcarbonyl group), carbonyl group to which the aforementioned "$C_2$-$C_6$ alkenyl group" is bound ($C_3$-$C_7$ alkenylcarbonyl group), carbonyl group to which the aforementioned "aryl group" is bound ("arylcarbonyl group"), carbonyl group to which the aforementioned "$C_1$-$C_6$ alkoxy group" is bound ($C_2$-$C_7$ alkoxycarbonyl group) or carbonyl group to which the aforementioned "$C_1$-$C_6$ alkylthio group" is bound ($C_2$-$C_7$ alkylthiocarbonyl group), preferably a formyl group, $C_2$-$C_5$ alkylcarbonyl group, $C_3$-$C_5$ alkenylcarbonyl group, benzoyl group, naphthoyl group, $C_2$-$C_5$ alkoxycarbonyl group or $C_2$-$C_5$ alkylthiocarbonyl group, more preferably a formyl group, $C_2$-$C_5$ alkylcarbonyl group, benzoyl group or $C_2$-$C_5$ alkoxycarbonyl group, particularly preferably an acetyl group, methoxycarbonyl group, ethoxycarbonyl group or benzoyl group and most preferably an acetyl group.

In compounds (Ia), (Ib) and (Ic) of the present invention, a "$C_2$-$C_7$ alkoxy-carbonyl group" is an alkoxycarbonyl group having 2 to 7 carbon atoms, including for example a methoxycarbonyl group, ethoxycarbonyl group or propoxycarbonyl group, wherein an alkoxy portion thereof may be linear or branched, preferably an alkoxy-carbonyl group having 2 to 4 carbon atoms and more preferably a methoxycarbonyl group.

In compounds (Ia), (Ib) and (Ic) of the present invention, a "$C_1$-$C_6$ alkyl group which may be substituted with 1 to 3 of the same or different halogen atoms" is, in addition to the aforementioned "$C_1$-$C_6$ alkyl groups", the aforementioned "$C_1$-$C_6$ alkyl group" substituted with 1 to 3 of the same or different aforementioned "halogen atoms", including for example a trifluoromethyl group, trichloromethyl group, difluoromethyl group, dichloromethyl group, dibromomethyl group, fluoromethyl group, chloromethyl group, bromomethyl group, iodomethyl group, 2,2,2-trichloroethyl group, 2,2,2-tri-fluoroethyl group, 2-bromoethyl group, 2-chloroethyl group, 2-fluoroethyl group, 3-chloropropyl group, 3,3,3-trifluoropropyl group, 4-fluorobutyl group, 3-fluoro-2-methylpropyl group, 3,3,3-trifluoro-2-methylpropyl group or 6,6,6-trichlorohexyl group, preferably the aforementioned "$C_1$-$C_4$ alkyl group" which may be substituted with 1 to 3 of the same or different aforementioned "halogen atoms", more preferably the aforementioned "$C_1$-$C_3$ alkyl group" which may be substituted with 1 to 3 of the same or different aforementioned "fluorine atoms or chlorine atoms", still more preferably a methyl group, ethyl group, propyl group, chloromethyl group or trifluoromethyl group and particularly preferably a methyl group, ethyl group or trifluoromethyl group.

In compounds (Ia), (Ib) and (Ic) of the present invention, a "N-hydroxyalkanimidoyl group in which a hydrogen atom of the hydroxyl group may be substituted with a substituent selected from the group consisting of a $C_1$-$C_6$ alkyl group, $C_2$-$C_6$ alkenyl group, $C_2$-$C_6$ alkynyl group, aralkyl group, aryl group and heteroaryl group" may be, in addition to a hydroxyalkanimidoyl group having 1 to 6 carbon atoms, including for example a hydroxyiminomethyl group, N-hydroxyethanimidoyl group, N-hydroxypropanimidoyl group or N-hydroxybutanimidoyl group, a group in which the hydroxyl group is substituted with the aforementioned "$C_1$-$C_6$ alkyl group", the aforementioned "$C_2$-$C_6$ alkenyl group", the aforementioned "$C_2$-$C_6$ alkynyl group", the aforementioned "aralkyl group", the aforementioned "aryl group" or the aforementioned "heteroaryl group", including for example a methoxyiminomethyl group, N-methoxyethanimidoyl group, N-ethoxyethanimidoyl group, N-butoxyethanimidoyl group, N-allyloxyethanimidoyl group, N-propargyloxyethanimidoyl group, N-benzyloxyethanimidoyl group, N-phenoxyethanimidoyl group, N-pyridyloxyethanimidoyl group, N-methoxypropanimidoyl group, N-methoxybutanimidoyl group or N-methoxyhexanimidoyl group, preferably a N-hydroxyalkaneimidoyl group having 1 to 4 carbon atoms in which a hydrogen atom of the hydroxyl group may be substituted with a substituent selected from the group consisting of a $C_1$-$C_6$ alkyl group and phenyl group, more preferably a hydroxyiminomethyl group, N-hydroxyethanimidoyl group, methoxyiminomethyl group, N-methoxyethanimidoyl group or N-ethoxyethanimidoyl group and particularly preferably a methoxyiminomethyl group or N-methoxyethanimidoyl group.

In compounds (Ia), (Ib) and (Ic) of the present invention, a "$C_1$-$C_6$ alkyl group which may be substituted with 1 to 3 of the same or different substituents selected from the group consisting of a halogen atom, $C_1$-$C_6$ alkoxy group, $C_1$-$C_6$ alkylthio group and phenoxy group" of $R^1$ and the like may be, in addition to the aforementioned "$C_1$-$C_6$ alkyl group which may be substituted with 1 to 3 of the same or different halogen atoms", the aforementioned "$C_1$-$C_6$ alkyl group" which is substituted with 1 to 3 of the same or different aforementioned "$C_1$-$C_6$ alkoxy groups", including for example a methoxymethyl group, ethoxymethyl group, ethoxyethyl group or propoxymethyl group, the aforementioned "$C_1$-$C_6$ alkyl group" which is substituted with 1 to 3 of the same or different aforementioned "$C_1$-$C_6$ alkylthio groups", including for example a methylthiomethyl group, ethylthiomethyl group or ethylthioethyl group, or the aforementioned "$C_1$-$C_6$ alkyl group" which is substituted with a phenoxy group, including for example a phenoxymethyl group or phenoxyethyl group, and further includes the aforementioned "$C_1$-$C_6$ alkyl group" which is substituted with 2 to 3 types of substituents selected from the group consisting of the aforementioned halogen atom, the aforementioned $C_1$-$C_6$ alkoxy group, the aforementioned $C_1$-$C_6$ alkylthio group and phenoxy group, including for example a 2-methoxy-1-chloroethyl group, 3-phenoxy-2-bromo-2-methoxypropyl group, 3-phenoxy-2-bromo-2-methylthiopropyl group, preferably a methyl group, ethyl group, propyl group, methoxymethyl group, ethoxymethyl group, phenoxymethyl group or methylthiomethyl group and more preferably a methyl group or ethyl group.

In compounds (Ia), (Ib) and (Ic) of the present invention, a "$C_1$-$C_6$ alkyl group which may be substituted with 1 to 3 of the same or different substituents selected from the group consisting of a halogen atom, $C_1$-$C_6$ alkoxy group, hydroxyl group, $C_2$-$C_7$ alkoxycarbonyl group and phenoxy group" in X and the like may be, in addition to the aforementioned "$C_1$-$C_6$ alkyl group which may be substituted with 1 to 3 of the same or different halogen atoms", the aforementioned "$C_1$-$C_6$ alkyl group" which is substituted with 1 to 3 of the same or different aforementioned "$C_1$-$C_6$ alkoxy groups", including for example a methoxymethyl group, ethoxymethyl group, ethoxyethyl group or propoxymethyl group, the aforementioned "$C_1$-$C_6$ alkyl group" which is substituted with 1 to 3 hydroxyl groups such as a hydroxymethyl group, 2-hydroxyethyl group or 3-hydroxypropyl group, the aforementioned "$C_1$-$C_6$ alkyl group" which is substituted with 1 to 3 of the same or different aforementioned "$C_2$-$C_7$ alkoxycarbonyl groups", including for example a methoxycarbonylmethyl group, ethoxycarbonylmethyl group, 2-(methoxycarbonyl)ethyl group, or the aforementioned "$C_1$-$C_6$ alkyl group" which is substituted with a phenoxy group, including for example a phenoxymethyl group or phenoxyethyl group, and further includes the aforementioned "$C_1$-$C_6$ alkyl group" which is substituted with 2 to 3 types of substituents selected from the group consisting of the aforementioned halogen atom, the aforementioned $C_1$-$C_6$ alkoxy group, hydroxyl group, the aforementioned $C_2$-$C_7$ alkoxycarbonyl group and phenoxy group, including for example a 2-methoxy-1-chloroethyl group, 2-hydroxy-1-chloroethyl group, 3-phenoxy-2-bromo-2-methoxycarbonylpropyl group, preferably a methyl group, ethyl group, propyl group, methoxymethyl group, ethoxymethyl group, phenoxymethyl group, methylthiomethyl group, methoxycarbonylmethyl group or ethoxycarbonylmethyl group and more preferably a methyl group or ethyl group.

In compounds (Ia), (Ib) and (Ic) of the present invention, a "$C_2$-$C_6$ alkenyl group which may be substituted with 1 to 3 of the same or different substituents selected from the group consisting of a halogen atom, $C_1$-$C_6$ alkoxy group, $C_2$-$C_7$ alkoxycarbonyl group and phenoxy group" in X and the like may be, in addition to the aforementioned "$C_2$-$C_6$ alkenyl group", the aforementioned "$C_2$-$C_6$ alkenyl group" which is substituted with 1 to 3 of the same or different halogen atoms, including for example a 3-chloroallyl group or 4-bromo-2-butenyl group, the aforementioned "$C_2$-$C_6$ alkenyl group" which is substituted with 1 to 3 of the same or different aforementioned "$C_1$-$C_6$ alkoxy groups", including for example a 3-methoxy-2-propenyl group or 4-ethoxy-3-butenyl group, the aforementioned "$C_2$-$C_6$ alkenyl group" which is substituted with 1 to 3 of the same or different aforementioned "$C_2$-$C_7$ alkoxycarbonyl groups", including for example a methoxycarbonylvinyl group, 3-(ethoxycarbonyl)-2-propenyl group or 4-(methoxycarbonyl)-2-butenyl group, or the aforementioned "$C_2$-$C_6$ alkenyl group" which is substituted with a phenoxy group, including for example a 3-phenoxy-2-butenyl group, and further includes the aforementioned "$C_2$-$C_6$ alkenyl group" which is substituted with 2 to 3 types of substituents selected from the group consisting of the aforementioned halogen atom, the aforementioned $C_1$-$C_6$ alkoxy group, the aforementioned $C_2$-$C_7$ alkoxycarbonyl group and phenoxy group, including for example a 4-methoxy-3-chloro-2-butenyl group, 4-methoxycarbonyl-3-chloro-2-butenyl group or 4-phenoxy-3-chloro-2-butenyl group, preferably a vinyl group, allyl group, isopropenyl group, but-1-en-1-yl group, 3-chloroallyl group, 4-bromo-2-butenyl group, methoxycarbonylvinyl group or 4-methoxycarbonylbutenyl group and more preferably an allyl group or isopropenyl group.

In compounds (Ia), (Ib) and (Ic) of the present invention, a "$C_2$-$C_6$ alkynyl group which may be substituted with 1 to 3 of the same or different substituents selected from the group consisting of a halogen atom, $C_1$-$C_6$ alkoxy group and phenoxy group" in X and the like may be, in addition to the aforementioned "$C_2$-$C_6$ alkynyl group", the aforementioned "$C_2$-$C_6$ alkynyl group" which is substituted with 1 to 3 same or different halogen atoms, including for example a 3-chloro-2-propynyl group or 4-bromo-2-butynyl group, the aforementioned "$C_2$-$C_6$ alkynyl group" which is substituted with 1 to 3 of the same or different aforementioned "$C_1$-$C_6$ alkoxy groups", including for example a 3-methoxy-2-propynyl group or 4-ethoxy-3-butynyl group, or the aforementioned "$C_2$-$C_6$ alkynyl group" which is substituted with a phenoxy group, including for example a 3-phenoxy-2-butynyl group, and further includes the aforementioned "$C_2$-$C_6$ alkynyl group" which is substituted with 2 to 3 types of substituents selected from the group consisting of the aforementioned halogen atom, the aforementioned $C_1$-$C_6$ alkoxy group and phenoxy group, including for example a 4-methoxy-4-chloro-2-butynyl group or 4-phenoxy-4-chloro-2-butynyl group, preferably an ethynyl group, prop-1-yn-1-yl group, 3-chloro-2-propynyl group, 3-methoxy-2-propynyl group, 4-methoxy-4-chloro-2-butynyl group or 4-phenoxy-4-chloro-2-butynyl group and more preferably an ethynyl group or prop-1-yn-1-yl group.

In compounds (Ia), (Ib) and (Ic) of the present invention, an "amino group which may be substituted with 1 to 2 of the same or different $C_1$-$C_6$ alkyl groups or acyl groups" in X and the like is, in addition to an amino group, an amino group which is substituted with 1 to 2 of the same or different aforementioned "$C_1$-$C_6$ alkyl groups" or with 1 to 2 of the same or different aforementioned "acyl groups", preferably an amino group which is substituted with 1 or 2 of the same or different aforementioned "$C_1$-$C_4$ alkyl groups" or with 1 or 2 of the same or different aforementioned "acyl groups" and more preferably a dimethylamino group, diethylamino group or acetylamino group.

In compounds (Ia), (Ib) and (Ic) of the present invention, a "$C_1$-$C_6$ alkylidene group" which $R^3$ and $R^4$ together form and the like is for example a linear or branched alkylidene group having 1 to 6 carbon atoms, including for example a methylidene group (methylene group), ethylidene group, propylidene group or isopropylidene group, preferably a linear or branched alkylidene group having 1 to 4 carbon atoms and particularly preferably a methylidene group (methylene group).

In compounds (Ia), (Ib) and (Ic) of the present invention, an "aryl group which may be substituted with 1 to 6 of the same or different substituents selected from the group consisting of a halogen atom, $C_1$-$C_6$ alkyl group which may be substituted with 1 to 3 of the same or different halogen atoms, $C_1$-$C_6$ alkoxy group, amino group which may be substituted with 1 to 2 same or different $C_1$-$C_6$ alkyl groups or acyl groups, nitro group, cyano group, hydroxyl group, mercapto group and $C_1$-$C_6$ alkylthio group" in $R^1$ and the like may be, in addition to the aforementioned "aryl group", the aforementioned "aryl group" which is substituted with 1 to 6 of the same or different aforementioned halogen atoms, the aforementioned "aryl group" which is substituted with 1 to 6 of the same or different aforementioned "$C_1$-$C_6$ alkyl groups which may be substituted with 1 to 3 of the same or different halogen atoms", the aforementioned "aryl group" which is substituted with 1 to 6 of the same or different aforementioned "$C_1$-$C_6$ alkoxy groups", the aforementioned "aryl group" which is substituted with 1 to 6 of the same or different aforementioned "amino groups which may be substituted with 1 to 2 of the same or different $C_1$-$C_2$ alkyl groups or acyl groups", the aforementioned "aryl group" which is substituted with 1 to 6 nitro groups, the aforementioned "aryl group" which is substituted with 1 to 6 cyano groups or the aforementioned "aryl group" which is substituted with 1 to 6 hydroxyl groups, the aforementioned "aryl group" which is substituted with 1 to 6 mercapto groups or the aforementioned "aryl group" which is substituted with 1 to 6 of the same or different aforementioned "$C_1$-$C_6$ alkylthio groups", and further includes the aforementioned "aryl group" which is substituted with 2 to 6 types of substituents selected from the group consisting of the aforementioned halogen atom, the aforementioned "$C_1$-$C_6$ alkyl group which may be substituted with 1 to 3 of the same or different halogen atoms", the aforementioned "$C_1$-$C_6$ alkoxy group", the aforementioned "amino group which may be substituted with 1 to 2 of the same or different $C_1$-$C_6$ alkyl groups or acyl groups", nitro group, cyano group, hydroxyl group, mercapto group and the aforementioned "$C_1$-$C_6$ alkylthio group", preferably a phenyl group, 1-naphthyl group, 2-naphthyl group, 4-fluorophenyl group, 4-chlorophenyl group, 3-methoxyphenyl group, 3-cyanophenyl group, 2-methylthiophenyl group or 2-trifluoromethylphenyl group and more preferably a phenyl group, 4-fluorophenyl group or 4-chlorophenyl group.

In compounds (Ia), (Ib) and (Ic) of the present invention, a "heteroaryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group" in $R^1$ and the like may be, in addition to the aforementioned "heteroaryl group", the aforementioned "heteroaryl group" which is substituted with 1 to 6 of the same or different halogen atoms, the aforementioned "heteroaryl group" which is substituted with 1 to 6 of the same or different aforementioned "$C_1$-$C_6$ alkyl groups which may be substituted with 1 to 3 of the same or different halogen atoms" or the aforementioned "heteroaryl group" which is substituted with 1 to 6 of the same or different aforementioned "$C_1$-$C_6$ alkoxy groups", and further includes the aforementioned "heteroaryl group" which is substituted with 2 to 6 types of substituents selected from the group consisting of the aforementioned halogen atom, the aforementioned "$C_1$-$C_6$ alkyl group" and the aforementioned "$C_1$-$C_6$ alkoxy group", preferably a furyl group, thienyl group, oxazolyl group, pyridyl group, benzofuranyl group, isobenzofuranyl group, 5-bromofuryl group, 6-chloropyridyl group, 4-trifluoromethylpyridyl group, 3-fluorothienyl group or 3-methoxythienyl group and more preferably a furyl group or thienyl group.

In compounds (Ia), (Ib) and (Ic) of the present invention, an "aralkyl group which may be substituted with 1 to 6 of the same or different substituents selected from the group consisting of a halogen atom, $C_1$-$C_6$ alkyl group which may be substituted with 1 to 3 of the same or different halogen atoms, $C_1$-$C_6$ alkoxy group, amino group which may be substituted with 1 to 2 of the same or different $C_1$-$C_6$ alkyl groups or acyl groups, nitro group, cyano group, hydroxyl group, mercapto group and $C_1$-$C_6$ alkylthio group" in $R^1$ and the like may be, in addition to the aforementioned "aralkyl group", the aforementioned "aralkyl group" which is substituted with 1 to 6 of the same or different halogen atoms, the aforementioned "aralkyl group" which is substituted with 1 to 6 of the same or different aforementioned "$C_1$-$C_6$ alkyl groups which may be substituted with 1 to 3 of the same or different halogen atoms", the aforementioned "aralkyl group" which is substituted with 1 to 6 of the same or different aforementioned "$C_1$-$C_6$ alkoxy groups", the aforementioned "aralkyl group" which is substituted with 1 to 6 of the same or different aforementioned "amino groups which may be substituted with 1 to 2 of the same or different $C_1$-$C_6$ alkyl groups or acyl groups", the aforementioned "aralkyl group" which is substituted with 1 to 6 nitro groups, the aforementioned "aralkyl group" which is substituted with 1 to 6 cyano groups, the aforementioned "aralkyl group" which is substituted with 1 to 6 hydroxyl groups, the aforementioned "aralkyl group" which is substituted with 1 to 6 mercapto groups or the aforementioned "aralkyl group" which is substituted with 1 to 6 of the same or different aforementioned "$C_1$-$C_6$ alkylthio groups", and further includes the aforementioned "aralkyl group" which is substituted with 2 or more types of substituents selected from the group consisting of the aforementioned halogen atom, the aforementioned "$C_1$-$C_6$ alkyl group which may be substituted with 1 to 3 of the same or different halogen atoms", the aforementioned "$C_1$-$C_6$ alkoxy group", the aforementioned "amino group which may be substituted with 1 or 2 of the same or different $C_1$-$C_6$ alkyl groups or acyl groups", nitro group, cyano group, hydroxyl group, mercapto group and the aforementioned "$C_1$-$C_6$ alkylthio group", in which in a case where the aralkyl group has a substituent group(s), the substituent(s) may substitute either one of or both of the aryl ring and the alkyl group, preferably a benzyl group, diphenylmethyl group, 1-phenethyl group, 2-phenethyl group, 4-chlorobenzyl group, 3-cyanobenzyl group or 4-methylthio-2-phenethyl group and more preferably a benzyl group.

In compounds (Ia), (Ib) and (Ic) of the present invention, a "$C_3$-$C_{10}$ cycloalkyl ring formed together with the carbon atom to which they are bound, which may be substituted with 1 to 3 of the same or different substituents selected from the group consisting of a halogen atom, $C_1$-$C_6$ alkyl group, $C_1$-$C_6$ alkoxy group and phenoxy group" in $R^1$ and $R^2$, and the like may be, in addition to the aforementioned "$C_3$-$C_{10}$ cycloalkyl ring", for example the aforementioned "$C_3$-$C_{10}$ cycloalkyl ring" which is substituted with 1 to 3 of the same or different halogen atoms, the aforementioned "$C_3$-$C_{10}$ cycloalkyl ring" which is substituted with 1 to 3 of the same or different aforementioned "$C_1$-$C_6$ alkyl groups", the aforementioned "$C_3$-$C_{10}$ cycloalkyl ring" which is substituted with 1 to 3 of the same or different aforementioned "$C_1$-$C_6$ alkoxy groups", or the aforementioned "$C_3$-$C_{10}$ cycloalkyl ring" which is substituted with 1 to 3 of the same or different phenoxy groups, and further includes the aforementioned "$C_3$-$C_{10}$ cycloalkyl ring" which is substituted with 2 to 3 types of substituents selected from the group consisting of the aforementioned halogen atom, the aforementioned "$C_1$-$C_6$ alkyl group", the aforementioned "$C_1$-$C_6$ alkoxy group" and phenoxy group, preferably a cyclobutyl ring, cyclopentyl ring, cyclohexyl ring, 2-chlorocyclopentyl ring, 4-methylcyclohexyl ring, 3-methoxycyclohexyl ring or 3-phenoxycyclohexyl ring and more preferably a cyclohexyl ring.

In compounds (Ia), (Ib) and (Ic) of the present invention, X can be substituted at 1 to 4 arbitrary substitutable positions on the isoquinoline ring, and in a case where 2 to 4 of Xs are present (in a case where n is 2 or more), they may be the same or different.

In compounds (Ia), (Ib) and (Ic) of the present invention, Y can be substituted at 1 to 6 arbitrary substitutable positions on the quinoline ring, and in a case where 2 to 6 of Ys are present (in a case where m is 2 or more), they may be the same or different.

Compounds (Ia), (Ib) or (Ic) of the present invention can be converted to salts, including for example mineral salts such as a hydrochloride, sulfate and nitrate; phosphates; sulfonates such as a methanesulfonate, ethanesulfonate, benzenesulfonate and p-toluenesulfonate; or organic carboxylates such as an acetate, benzoate, oxalate, fumalate and salicylate (preferably hydrochlorides, sulfates, nitrates, methanesulfonates, oxalates, fumarates or salicylates). These salts are included in the scope of the present invention so long as they can be used as a soil treating agent or as a seed treating agent.

Compound (Ia), (Ib) or (Ic) of the present invention or salts thereof can be converted to solvates, and these solvates are also included in the scope of the present invention. The solvates are preferably hydrates.

Compound (Ia), (Ib) or (Ic) of the present invention may have compounds having asymmetric carbons, and in such cases the invention of the present application also includes one of the optically active forms or a mixture containing several optically active forms at an arbitrary ratio.

In compounds (Ia), (Ib) or (Ic) of the present invention, $R^1$ and $R^2$ are, (1a) preferably a $C_1$-$C_6$ alkyl group which may be substituted with 1 to 3 of the same or different substituents selected from the group consisting of a halogen atom, $C_1$-$C_6$ alkoxy group and phenoxy group or an aryl group which may be substituted with 1 to 6 of the same or different substituents selected from the group consisting of a halogen atom, $C_1$-$C_6$ alkyl group, $C_1$-$C_6$ alkoxy group and hydroxyl group, (1b) more preferably $C_1$-$C_6$ alkyl group which may be substituted with 1 to 3 of the same or different halogen atoms, or phenyl group which may be substituted with 1 to 5 of the same or different halogen atoms, (1c) still more preferably a methyl group, ethyl group, propyl group, trifluoromethyl group, trifluoroethyl group, phenyl group, fluorophenyl group or chlorophenyl group, $R^3$ and $R^4$ are, (2a) preferably a hydrogen atom, $C_1$-$C_4$ alkyl group, halogen atom, methoxy group, ethoxy group or hydroxyl group, (2b) more preferably a hydrogen atom, methyl group, ethyl group, fluorine atom or chlorine atom, (2c) still more preferably a hydrogen atom, methyl group or fluorine atom, Xn is, (3a) preferably such that X is a halogen atom; $C_1$-$C_6$ alkyl group; $C_2$-$C_6$ alkynyl group; aryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group; heteroaryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group; cyano group; or N-hydroxy-$C_1$-$C_6$ alkanimidoyl group in which a hydrogen atom of the hydroxyl group may be substituted with a substituent selected from the group consisting of a $C_1$-$C_6$ alkyl group and phenyl group, and n is an integer of 0 to 2, (3b) more preferably such that X is a halogen atom; $C_1$-$C_4$ alkyl group; $C_2$-$C_3$ alkynyl group; phenyl group which may be substituted with 1 to 2 of the same or different substituents selected from the group consisting of a fluorine atom, chlorine atom, $C_1$-$C_2$ alkyl group which may be substituted with 1 to 3 fluorine atoms and $C_1$-$C_2$ alkoxy group; furyl group, thienyl group, oxazolyl group or pyridyl group, each of which may be substituted with 1 to 3 of the same or different substituents selected from the group consisting of a fluorine atom, chlorine atom, $C_1$-$C_2$ alkyl group which may be substituted with 1 to 3 of fluorine atoms and $C_1$-$C_2$ alkoxy group; cyano group; or N-hydroxy-$C_1$-$C_2$ alkanimidoyl group in which a hydrogen atom of the hydroxyl group may be substituted with a substituent selected from the group consisting of a $C_1$-$C_2$ alkyl group and phenyl group, and n is an integer of 0 to 2, (3c) still more preferably such that X is a fluorine atom, chlorine atom, bromine atom, methyl group, ethynyl group, furyl group, thienyl group, cyano group, methoxyethanimidoyl group, ethoxyethanimidoyl group or phenoxyethanimidoyl group, and n is an integer of 0 or 1, Ym is,
(4a) preferably such that Y is a fluorine atom, chlorine atom, bromine atom, $C_1$-$C_3$ alkyl group, methoxy group, ethoxy group or hydroxyl group and m is an integer of 0 to 2,
(4b) more preferably such that Y is a fluorine atom, chlorine atom or methyl group, and m is an integer of 0 or 1,
(4c) still more preferably such that Y is a methyl group, and m is an integer of 0 or 1.

In addition, compounds obtained by combining $R^1$ and $R^2$ selected from (1a)-(1c), $R^3$ and $R^4$ selected from (2a)-(2c), Xn selected from (3a)-(3c) and Ym selected from (4a)-(4c) are also preferable, for example, (A1) a compound where $R^1$ and $R^2$ are a $C_1$-$C_6$ alkyl group which may be substituted with 1 to 3 of the same or different substituents selected from the group consisting of a halogen atom, $C_1$-$C_6$ alkoxy group and phenoxy group; or an aryl group which may be substituted with 1 to 6 of the same or different substituents selected from the group consisting of a halogen atom, $C_1$-$C_6$ alkyl group, $C_1$-$C_6$ alkoxy group and hydroxyl group, $R^3$ and $R^4$ are a hydrogen atom, $C_1$-$C_4$ alkyl group, halogen atom, methoxy group, ethoxy group or hydroxyl group, X is a halogen atom; $C_1$-$C_6$ alkyl group; $C_2$-$C_6$ alkynyl group; aryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group; heteroaryl group which may be substituted with 1 to 6 of the same or different substituents selected from the group consisting of a halogen atom, $C_1$-$C_6$ alkyl group which may be substituted with 1 to 3 of the same or different halogen atoms and $C_1$-$C_6$ alkoxy group; cyano group; or N-hydroxy-$C_1$-$C_6$ alkanimidoyl group in which a hydrogen atom of the hydroxyl group may be substituted with a substituent selected from the group consisting of a $C_1$-$C_6$ alkyl group and phenyl group, and n is an integer of 0 to 2, Y is a fluorine atom, chlorine atom, bromine atom, $C_1$-$C_3$ alkyl group, methoxy group, ethoxy group or hydroxyl group, and m is an integer of 0 to 2, (A2) a compound where $R^1$ and $R^2$ are a $C_1$-$C_6$ alkyl group which may be substituted with 1 to 3 of the same or different halogen atoms; or a phenyl group which may be substituted with 1 to 5 of the same or different halogen atoms, $R^3$ and $R^4$ are a hydrogen atom, methyl group, ethyl group, fluorine atom or chlorine atom, X is a halogen atom; $C_1$-$C_4$ alkyl group; $C_2$-$C_3$ alkynyl group; phenyl group which may substituted with 1 to 2 of the same or different substituents selected from the group consisting of a fluorine atom, chlorine atom, $C_1$-$C_2$ alkyl group which may be substituted with 1 to 3 fluorine atoms and $C_1$-$C_2$ alkoxy group; furyl group, thienyl group, oxazolyl group or pyridyl group, which (the 4 groups) may be substituted with 1 to 3 of the same or different substituents selected from the group consisting of a fluorine atom, chlorine atom, $C_1$-$C_2$ alkyl group which may be substituted with 1 to 3 of fluorine atoms and $C_1$-$C_2$ alkoxy group; cyano group; or N-hydroxy-$C_1$-$C_2$ alkanimidoyl group in which a hydrogen atom of the hydroxyl group may be substituted with a substituent selected from the group consisting of a $C_1$-$C_2$ alkyl group and phenyl group, and n is an integer of 0 to 2, Y is a fluorine atom, chlorine atom or methyl group, and m is an integer of 0 or 1, or (A3) a compound where $R^1$ and $R^2$ are a methyl group, ethyl group, propyl group, trifluoromethyl group, trifluoroethyl group, phenyl group, fluorophenyl group or chlorophenyl group, $R^3$ and $R^4$ are a hydrogen atom, methyl group or fluorine atom, X is a fluorine atom, chlorine atom, bromine atom, methyl group, ethynyl group, furyl group, thienyl group, cyano group, methoxyethanimidoyl group, ethoxyethanimidoyl group or phenoxyethanimidoyl group, and n is an integer of 0 or 1, Y is a methyl group, and m is an integer of 0 or 1, can be mentioned.

Concerning compounds (Ia), (Ib) or (Ic) of the present invention, representative compounds are indicated in the following tables, but the present invention is not limited to these compounds.

In the following tables, "Me" indicates a methyl group, "Et" an ethyl group, "Pr" a propyl group, "iPr" an isopropyl group, "iBu" an isobutyl group, "tBu" a t-butyl group, "ipen" an isopentyl group, "Vinyl" a vinyl group, "Allyl" an allyl group, "Ethynyl" an ethynyl group, "Ph" a phenyl group, "4FPh" a 4-fluorophenyl group, "FUR" a furyl group, "2THI" a 2-thienyl group, "OXA" an oxazolyl group, "Ac" an acetyl group, "HEtIMD" a N-hydroxyethanimidoyl group, "MeEtIMD" a N-methoxyethanimidoyl group, "3PYD" a 3-pyridyl group, "Bn" a benzyl group, "Ms" a methanesulfonyl group, "cBu" a cyclobutane ring which $R^1$ and $R^2$ or $R^3$ and $R^4$ form together with the carbon atom to which they are bound, "cPen" a cyclopentyl ring which $R^1$ and $R^2$ or $R^3$ and $R^4$ form together with the carbon atom to which they are bound, "3-MecPen" a 3-methylcyclopentyl ring which $R^1$ and $R^2$ or $R^3$ and $R^4$ form together with the carbon atom to which they are bound, "cHex" a cyclohexyl ring which $R^1$ and $R^2$ or $R^3$ and $R^4$ form together with the carbon atom to which they are bound, "cHep" a cycloheptyl ring which $R^1$ and $R^2$ or $R^3$ and $R^4$ form together with the carbon atom to which they are bound, "O=" an oxo group which $R^3$ and $R^4$ together form, "$CH_2=$" a methylidene group which $R^3$ and $R^4$ together form, "H" in "Xn" and "Ym" indicates that n is 0 or m is 0, and blank in "type of salt" indicates that it is in free form.

TABLE 1

(Ia)

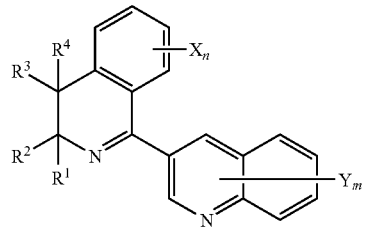

| Compound No. | R1, R2 | R3, R4 | Xn | Ym | Type of salt |
|---|---|---|---|---|---|
| 1-1 | Me, Me | H, H | H | H | |
| 1-2 | Me, Me | H, H | H | 2-F | |

TABLE 1-continued

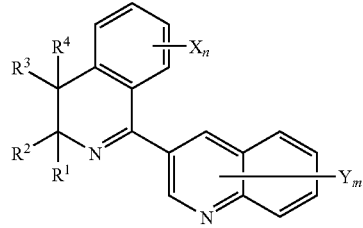

(Ia)

| Compound No. | R1, R2 | R3, R4 | Xn | Ym | Type of salt |
|---|---|---|---|---|---|
| 1-3 | Me, Me | H, H | H | 4-F | |
| 1-4 | Me, Me | H, H | H | 5-F | |
| 1-5 | Me, Me | H, H | H | 6-F | |
| 1-6 | Me, Me | H, H | H | 7-F | |
| 1-7 | Me, Me | H, H | H | 8-F | |
| 1-8 | Me, Me | H, H | H | 2-Cl | |
| 1-9 | Me, Me | H, H | H | 4-Cl | |
| 1-10 | Me, Me | H, H | H | 5-Cl | |
| 1-11 | Me, Me | H, H | H | 6-Cl | |
| 1-12 | Me, Me | H, H | H | 7-Cl | |
| 1-13 | Me, Me | H, H | H | 8-Cl | |
| 1-14 | Me, Me | H, H | H | 2-Me | |
| 1-15 | Me, Me | H, H | H | 4-Me | |
| 1-16 | Me, Me | H, H | H | 5-Me | |
| 1-17 | Me, Me | H, H | H | 6-Me | |
| 1-18 | Me, Me | H, H | H | 7-Me | |
| 1-19 | Me, Me | H, H | H | 8-Me | |
| 1-20 | Me, Me | H, H | H | 2-MeO | |
| 1-21 | Me, Me | H, H | H | 4-MeO | |
| 1-22 | Me, Me | H, H | H | 5-MeO | |
| 1-23 | Me, Me | H, H | H | 6-MeO | |
| 1-24 | Me, Me | H, H | H | 7-MeO | |
| 1-25 | Me, Me | H, H | H | 8-MeO | |
| 1-26 | Me, Me | H, H | H | 2-OH | |
| 1-27 | Me, Me | H, H | H | 4-OH | |
| 1-28 | Me, Me | H, H | H | 5-OH | |
| 1-29 | Me, Me | H, H | H | 6-OH | |
| 1-30 | Me, Me | H, H | H | 7-OH | |
| 1-31 | Me, Me | H, H | H | 8-OH | |
| 1-32 | Me, Me | H, H | 5-F | H | |
| 1-33 | Me, Me | H, H | 5-F | 4-F | |
| 1-34 | Me, Me | H, H | 5-F | 8-F | |
| 1-35 | Me, Me | H, H | 5-F | 4-Cl | |
| 1-36 | Me, Me | H, H | 5-F | 6-Cl | |
| 1-37 | Me, Me | H, H | 5-F | 4-MeO | |
| 1-38 | Me, Me | H, H | 5-F | 8-Me | |
| 1-39 | Me, Me | H, H | 5-F | 8-MeO | |
| 1-40 | Me, Me | H, H | 5-F | 8-OH | |
| 1-41 | Me, Me | H, H | 6-F | H | |
| 1-42 | Me, Me | H, H | 7-F | H | |
| 1-43 | Me, Me | H, H | 8-F | H | |
| 1-44 | Me, Me | H, H | 5-Cl | H | |
| 1-45 | Me, Me | H, H | 5-Cl | 4-F | |
| 1-46 | Me, Me | H, H | 5-Cl | 8-F | |
| 1-47 | Me, Me | H, H | 5-Cl | 4-Cl | |
| 1-48 | Me, Me | H, H | 5-Cl | 6-Cl | |
| 1-49 | Me, Me | H, H | 5-Cl | 4-Me | |
| 1-50 | Me, Me | H, H | 5-Cl | 8-Me | |
| 1-51 | Me, Me | H, H | 5-Cl | 8-MeO | |
| 1-52 | Me, Me | H, H | 5-Cl | 8-OH | |
| 1-53 | Me, Me | H, H | 6-Cl | H | |
| 1-54 | Me, Me | H, H | 7-Cl | H | |
| 1-55 | Me, Me | H, H | 8-Cl | H | |
| 1-56 | Me, Me | H, H | 5-Br | H | |
| 1-57 | Me, Me | H, H | 5-Br | 4-F | |
| 1-58 | Me, Me | H, H | 5-Br | 8-F | |
| 1-59 | Me, Me | H, H | 5-Br | 4-Cl | |
| 1-60 | Me, Me | H, H | 5-Br | 6-Cl | |
| 1-61 | Me, Me | H, H | 5-Br | 4-Me | |
| 1-62 | Me, Me | H, H | 5-Br | 8-Me | |
| 1-63 | Me, Me | H, H | 5-Br | 8-MeO | |
| 1-64 | Me, Me | H, H | 5-Br | 8-OH | |
| 1-65 | Me, Me | H, H | 6-Br | H | |
| 1-66 | Me, Me | H, H | 7-Br | H | |

TABLE 1-continued

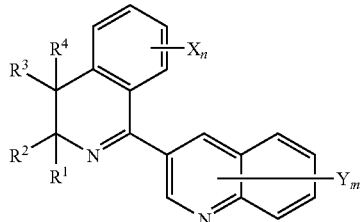

(Ia)

| Compound No. | R1, R2 | R3, R4 | Xn | Ym | Type of salt |
|---|---|---|---|---|---|
| 1-67 | Me, Me | H, H | 8-Br | H | |
| 1-68 | Me, Me | H, H | 5-I | H | |
| 1-69 | Me, Me | H, H | 5-Me | H | |
| 1-70 | Me, Me | H, H | 6-Me | H | |
| 1-71 | Me, Me | H, H | 7-Me | H | |
| 1-72 | Me, Me | H, H | 8-Me | H | |
| 1-73 | Me, Me | H, H | 5-Et | H | |
| 1-74 | Me, Me | H, H | 6-Et | H | |
| 1-75 | Me, Me | H, H | 7-Et | H | |
| 1-76 | Me, Me | H, H | 8-Et | H | |
| 1-77 | Me, Me | H, H | 5-Pr | H | |
| 1-78 | Me, Me | H, H | 6-Pr | H | |
| 1-79 | Me, Me | H, H | 7-Pr | H | |
| 1-80 | Me, Me | H, H | 8-Pr | H | |
| 1-81 | Me, Me | H, H | 5-Vinyl | H | |
| 1-82 | Me, Me | H, H | 6-Vinyl | H | |
| 1-83 | Me, Me | H, H | 7-Vinyl | H | |
| 1-84 | Me, Me | H, H | 8-Vinyl | H | |
| 1-85 | Me, Me | H, H | 5-Etynyl | H | |
| 1-86 | Me, Me | H, H | 6-Etynyl | H | |
| 1-87 | Me, Me | H, H | 7-Etynyl | H | |
| 1-88 | Me, Me | H, H | 8-Etynyl | H | |
| 1-89 | Me, Me | H, H | 5-Ph | H | |
| 1-90 | Me, Me | H, H | 6-Ph | H | |
| 1-91 | Me, Me | H, H | 7-Ph | H | |
| 1-92 | Me, Me | H, H | 8-Ph | H | |
| 1-93 | Me, Me | H, H | 5-FUR | H | |
| 1-94 | Me, Me | H, H | 5-2THI | H | |
| 1-95 | Me, Me | H, H | 5-3THI | H | |
| 1-96 | Me, Me | H, H | 5-(2-Cl-2THI) | H | |
| 1-97 | Me, Me | H, H | OXA | H | |
| 1-98 | Me, Me | H, H | 5-HEtIMD | H | |
| 1-99 | Me, Me | H, H | 5-MeMeIMD | H | |
| 1-100 | Me, Me | H, H | 5-MeEtIMD | H | |
| 1-101 | Me, Me | H, H | 5-EtEtIMD | H | |
| 1-102 | Me, Me | H, H | 5-PrEtIMD | H | |
| 1-103 | Me, Me | H, H | 5-tBuEtIMD | H | |
| 1-104 | Me, Me | H, H | 5-AllylEtIMD | H | |
| 1-105 | Me, Me | H, H | 5-BnEtIMD | H | |
| 1-106 | Me, Me | H, H | 5-PhEtIMD | H | |
| 1-107 | Me, Me | H, H | 5-MeO | H | |
| 1-108 | Me, Me | H, H | 6-MeO | H | |
| 1-109 | Me, Me | H, H | 7-MeO | H | |
| 1-110 | Me, Me | H, H | 8-MeO | H | |
| 1-111 | Me, Me | H, H | 5-NH2 | H | |
| 1-112 | Me, Me | H, H | 5-NHAc | H | |
| 1-113 | Me, Me | H, H | 5-CHO | H | |
| 1-114 | Me, Me | H, H | 5-Ac | H | |
| 1-115 | Me, Me | H, H | 5-CONHMe | H | |
| 1-116 | Me, Me | H, H | 5-CN | H | |
| 1-117 | Me, Me | H, H | 5,6-F2 | H | |
| 1-118 | Me, Me | H, H | 5,6-F2 | 4-F | |
| 1-119 | Me, Me | H, H | 5,6-F2 | 8-F | |
| 1-120 | Me, Me | H, H | 5,6-F2 | 4-Cl | |
| 1-121 | Me, Me | H, H | 5,6-F2 | 6-Cl | |
| 1-122 | Me, Me | H, H | 5,6-F2 | 4-Me | |
| 1-123 | Me, Me | H, H | 5,6-F2 | 8-Me | |
| 1-124 | Me, Me | H, H | 5,6-F2 | 8-MeO | |
| 1-125 | Me, Me | H, H | 5,6-F2 | 8-OH | |
| 1-126 | Me, Me | H, H | 5,6-Cl2 | H | |
| 1-127 | Me, Me | H, H | 5,6-Cl2 | 4-F | |
| 1-128 | Me, Me | H, H | 5,6-Cl2 | 8-F | |
| 1-129 | Me, Me | H, H | 5,6-Cl2 | 4-Cl | |
| 1-130 | Me, Me | H, H | 5,6-Cl2 | 6-Cl | |

TABLE 1-continued

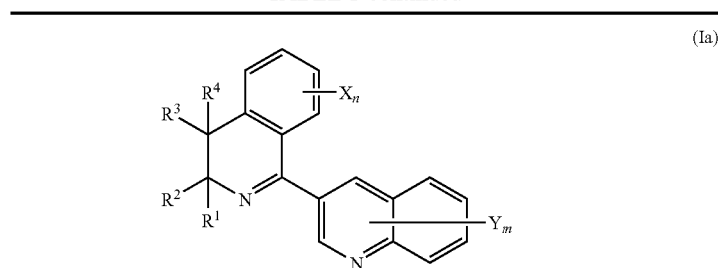

(Ia)

| Compound No. | R1, R2 | R3, R4 | Xn | Ym | Type of salt |
|---|---|---|---|---|---|
| 1-131 | Me, Me | H, H | 5,6-Cl2 | 4-Me | |
| 1-132 | Me, Me | H, H | 5,6-Cl2 | 8-Me | |
| 1-133 | Me, Me | H, H | 5,6-Cl2 | 8-MeO | |
| 1-134 | Me, Me | H, H | 5,6-Cl2 | 8-OH | |
| 1-135 | Me, Me | H, H | 5-F,7-Me | H | |
| 1-136 | Me, Me | H, H | 6-F,7-Me | H | |
| 1-137 | Me, Et | H, H | H | H | |
| 1-138 | Me, Et | H, H | H | 4-F | |
| 1-139 | Me, Et | H, H | H | 8-F | |
| 1-140 | Me, Et | H, H | H | 4-Cl | |
| 1-141 | Me, Et | H, H | H | 6-Cl | |
| 1-142 | Me, Et | H, H | H | 8-Cl | |
| 1-143 | Me, Et | H, H | H | 4-Me | |
| 1-144 | Me, Et | H, H | H | 8-Me | |
| 1-145 | Me, Et | H, H | H | 8-MeO | |
| 1-146 | Me, Et | H, H | H | 8-OH | |
| 1-147 | Me, Et | H, H | 5-F | H | |
| 1-148 | Me, Et | H, H | 6-F | H | |
| 1-149 | Me, Et | H, H | 7-F | H | |
| 1-150 | Me, Et | H, H | 5-Cl | H | |
| 1-151 | Me, Et | H, H | 6-Cl | H | |
| 1-152 | Me, Et | H, H | 7-Cl | H | |
| 1-153 | Me, Et | H, H | 5-Br | H | |
| 1-154 | Me, Et | H, H | 6-Br | H | |
| 1-155 | Me, Et | H, H | 7-Br | H | |
| 1-156 | Me, Et | H, H | 5-I | H | |
| 1-157 | Me, Et | H, H | 5-Me | H | |
| 1-158 | Me, Et | H, H | 5-Vinyl | H | |
| 1-159 | Me, Et | H, H | 5-Etynyl | H | |
| 1-160 | Me, Et | H, H | 5-Ph | H | |
| 1-161 | Me, Et | H, H | 5-FUR | H | |
| 1-162 | Me, Et | H, H | 5-2THI | H | |
| 1-163 | Me, Et | H, H | 5-3THI | H | |
| 1-164 | Me, Et | H, H | 5-(2-Cl-2THI) | H | |
| 1-165 | Me, Et | H, H | OXA | H | |
| 1-166 | Me, Et | H, H | 5-MeMeIMD | H | |
| 1-167 | Me, Et | H, H | 5-MeEtIMD | H | |
| 1-168 | Me, Et | H, H | 5-EtEIMD | H | |
| 1-169 | Me, Et | H, H | 5-AllylEtIMD | H | |
| 1-170 | Me, Et | H, H | 5-BnEtIMD | H | |
| 1-171 | Me, Et | H, H | 5-PhEtIMD | H | |
| 1-172 | Me, Et | H, H | 5-CN | H | |
| 1-173 | Me, Et | H, H | 5,6-F2 | H | |
| 1-174 | Me, Et | H, H | 5,6-Cl2 | H | |
| 1-175 | Me, Pr | H, H | H | H | |
| 1-176 | Me, Pr | H, H | H | 4-F | |
| 1-177 | Me, Pr | H, H | H | 8-F | |
| 1-178 | Me, Pr | H, H | H | 4-Cl | |
| 1-179 | Me, Pr | H, H | H | 6-Cl | |
| 1-180 | Me, Pr | H, H | H | 8-Cl | |
| 1-181 | Me, Pr | H, H | H | 4-Me | |
| 1-182 | Me, Pr | H, H | H | 8-Me | |
| 1-183 | Me, Pr | H, H | H | 8-MeO | |
| 1-184 | Me, Pr | H, H | H | 8-OH | |
| 1-185 | Me, Pr | H, H | 5-F | H | |
| 1-186 | Me, Pr | H, H | 6-F | H | |
| 1-187 | Me, Pr | H, H | 7-F | H | |
| 1-188 | Me, Pr | H, H | 5-Cl | H | |
| 1-189 | Me, Pr | H, H | 6-Cl | H | |
| 1-190 | Me, Pr | H, H | 7-Cl | H | |
| 1-191 | Me, Pr | H, H | 5-Br | H | |
| 1-192 | Me, Pr | H, H | 6-Br | H | |
| 1-193 | Me, Pr | H, H | 7-Br | H | |
| 1-194 | Me, Pr | H, H | 5-I | H | |

TABLE 1-continued

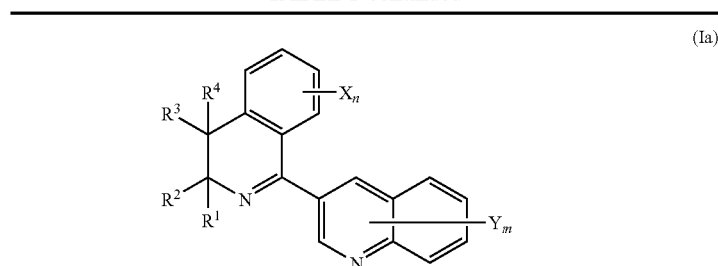

(Ia)

| Compound No. | R1, R2 | R3, R4 | Xn | Ym | Type of salt |
|---|---|---|---|---|---|
| 1-195 | Me, Pr | H, H | 5-Me | H | |
| 1-196 | Me, Pr | H, H | 5-Vinyl | H | |
| 1-197 | Me, Pr | H, H | 5-Etynyl | H | |
| 1-198 | Me, Pr | H, H | 5-Ph | H | |
| 1-199 | Me, Pr | H, H | 5-FUR | H | |
| 1-200 | Me, Pr | H, H | 5-2THI | H | |
| 1-201 | Me, Pr | H, H | 5-3THI | H | |
| 1-202 | Me, Pr | H, H | 5-(2-Cl-2THI) | H | |
| 1-203 | Me, Pr | H, H | OXA | H | |
| 1-204 | Me, Pr | H, H | 5-MeMeIMD | H | |
| 1-205 | Me, Pr | H, H | 5-MeEtIMD | H | |
| 1-206 | Me, Pr | H, H | 5-EtEtIMD | H | |
| 1-207 | Me, Pr | H, H | 5-AllylEtIMD | H | |
| 1-208 | Me, Pr | H, H | 5-BnEtIMD | H | |
| 1-209 | Me, Pr | H, H | 5-PhEtIMD | H | |
| 1-210 | Me, Pr | H, H | 5-CN | H | |
| 1-211 | Me, Pr | H, H | 5,6-F2 | H | |
| 1-212 | Me, Pr | H, H | 5,6-Cl2 | H | |
| 1-213 | Me, iPr | H, H | H | H | |
| 1-214 | Me, iPr | H, H | H | 4-F | |
| 1-215 | Me, iPr | H, H | H | 8-F | |
| 1-216 | Me, iPr | H, H | H | 4-Cl | |
| 1-217 | Me, iPr | H, H | H | 6-Cl | |
| 1-218 | Me, iPr | H, H | H | 8-Cl | |
| 1-219 | Me, iPr | H, H | H | 4-Me | |
| 1-220 | Me, iPr | H, H | H | 8-Me | |
| 1-221 | Me, iPr | H, H | H | 8-MeO | |
| 1-222 | Me, iPr | H, H | H | 8-OH | |
| 1-223 | Me, iPr | H, H | 5-F | H | |
| 1-224 | Me, iPr | H, H | 6-F | H | |
| 1-225 | Me, iPr | H, H | 7-F | H | |
| 1-226 | Me, iPr | H, H | 5-Cl | H | |
| 1-227 | Me, iPr | H, H | 6-Cl | H | |
| 1-228 | Me, iPr | H, H | 7-Cl | H | |
| 1-229 | Me, iPr | H, H | 5-Br | H | |
| 1-230 | Me, iPr | H, H | 6-Br | H | |
| 1-231 | Me, iPr | H, H | 7-Br | H | |
| 1-232 | Me, iPr | H, H | 5-I | H | |
| 1-233 | Me, iPr | H, H | 5-Me | H | |
| 1-234 | Me, iPr | H, H | 5-Vinyl | H | |
| 1-235 | Me, iPr | H, H | 5-Etynyl | H | |
| 1-236 | Me, iPr | H, H | 5-Ph | H | |
| 1-237 | Me, iPr | H, H | 5-FUR | H | |
| 1-238 | Me, iPr | H, H | 5-2THI | H | |
| 1-239 | Me, iPr | H, H | 5-3THI | H | |
| 1-240 | Me, iPr | H, H | 5-(2-Cl-2THI) | H | |
| 1-241 | Me, iPr | H, H | OXA | H | |
| 1-242 | Me, iPr | H, H | 5-MeMeIMD | H | |
| 1-243 | Me, iPr | H, H | 5-MeEtIMD | H | |
| 1-244 | Me, iPr | H, H | 5-EtEtIMD | H | |
| 1-245 | Me, iPr | H, H | 5-AllylEtIMD | H | |
| 1-246 | Me, iPr | H, H | 5-BnEtIMD | H | |
| 1-247 | Me, iPr | H, H | 5-PhEtIMD | H | |
| 1-248 | Me, iPr | H, H | 5-CN | H | |
| 1-249 | Me, iPr | H, H | 5,6-F2 | H | |
| 1-250 | Me, iPr | H, H | 5,6-Cl2 | H | |
| 1-251 | Me, iBu | H, H | H | H | |
| 1-252 | Me, iBu | H, H | H | 4-F | |
| 1-253 | Me, iBu | H, H | H | 8-F | |
| 1-254 | Me, iBu | H, H | H | 4-Cl | |
| 1-255 | Me, iBu | H, H | H | 6-Cl | |
| 1-256 | Me, iBu | H, H | H | 8-Cl | |
| 1-257 | Me, iBu | H, H | H | 4-Me | |
| 1-258 | Me, iBu | H, H | H | 8-Me | |

TABLE 1-continued

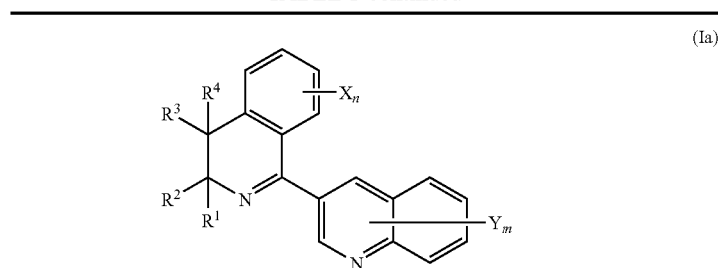

(Ia)

| Compound No. | R1, R2 | R3, R4 | Xn | Ym | Type of salt |
|---|---|---|---|---|---|
| 1-259 | Me, iBu | H, H | H | 8-MeO | |
| 1-260 | Me, iBu | H, H | H | 8-OH | |
| 1-261 | Me, iBu | H, H | 5-F | H | |
| 1-262 | Me, iBu | H, H | 6-F | H | |
| 1-263 | Me, iBu | H, H | 7-F | H | |
| 1-264 | Me, iBu | H, H | 5-Cl | H | |
| 1-265 | Me, iBu | H, H | 6-Cl | H | |
| 1-266 | Me, iBu | H, H | 7-Cl | H | |
| 1-267 | Me, iBu | H, H | 5-Br | H | |
| 1-268 | Me, iBu | H, H | 6-Br | H | |
| 1-269 | Me, iBu | H, H | 7-Br | H | |
| 1-270 | Me, iBu | H, H | 5-I | H | |
| 1-271 | Me, iBu | H, H | 5-Me | H | |
| 1-272 | Me, iBu | H, H | 5-Vinyl | H | |
| 1-273 | Me, iBu | H, H | 5-Etynyl | H | |
| 1-274 | Me, iBu | H, H | 5-Ph | H | |
| 1-275 | Me, iBu | H, H | 5-FUR | H | |
| 1-276 | Me, iBu | H, H | 5-2THI | H | |
| 1-277 | Me, iBu | H, H | 5-3THI | H | |
| 1-278 | Me, iBu | H, H | 5-(2-Cl-2THI) | H | |
| 1-279 | Me, iBu | H, H | OXA | H | |
| 1-280 | Me, iBu | H, H | 5-MeMeIMD | H | |
| 1-281 | Me, iBu | H, H | 5-MeEtIMD | H | |
| 1-282 | Me, iBu | H, H | 5-EtEtIMD | H | |
| 1-283 | Me, iBu | H, H | 5-AllylEtIMD | H | |
| 1-284 | Me, iBu | H, H | 5-BnEtIMD | H | |
| 1-285 | Me, iBu | H, H | 5-PhEtIMD | H | |
| 1-286 | Me, iBu | H, H | 5-CN | H | |
| 1-287 | Me, iBu | H, H | 5,6-F2 | H | |
| 1-288 | Me, iBu | H, H | 5,6-Cl2 | H | |
| 1-289 | Me, tBu | H, H | H | H | |
| 1-290 | Me, tBu | H, H | 5-F | H | |
| 1-291 | Me, tBu | H, H | 5-Cl | H | |
| 1-292 | Me, tBu | H, H | 5-Br | H | |
| 1-293 | Me, tBu | H, H | 5-I | H | |
| 1-294 | Me, tBu | H, H | 5-Me | H | |
| 1-295 | Me, tBu | H, H | 5-Vinyl | H | |
| 1-296 | Me, tBu | H, H | 5-Etynyl | H | |
| 1-297 | Me, tBu | H, H | 5-Ph | H | |
| 1-298 | Me, tBu | H, H | 5-FUR | H | |
| 1-299 | Me, tBu | H, H | 5-2THI | H | |
| 1-300 | Me, tBu | H, H | 5-3THI | H | |
| 1-301 | Me, tBu | H, H | 5-MeEtIMD | H | |
| 1-302 | Me, tBu | H, H | 5-EtEtIMD | H | |
| 1-303 | Me, tBu | H, H | 5-PhEtIMD | H | |
| 1-304 | Me, tBu | H, H | 5-CN | H | |
| 1-305 | Me, tBu | H, H | 5,6-F2 | H | |
| 1-306 | Me, tBu | H, H | 5,6-Cl2 | H | |
| 1-307 | Me, iPen | H, H | H | H | |
| 1-308 | Me, iPen | H, H | H | 4-F | |
| 1-309 | Me, iPen | H, H | H | 8-F | |
| 1-310 | Me, iPen | H, H | H | 4-Cl | |
| 1-311 | Me, iPen | H, H | H | 6-Cl | |
| 1-312 | Me, iPen | H, H | H | 8-Cl | |
| 1-313 | Me, iPen | H, H | H | 4-Me | |
| 1-314 | Me, iPen | H, H | H | 8-Me | |
| 1-315 | Me, iPen | H, H | H | 8-MeO | |
| 1-316 | Me, iPen | H, H | H | 8-OH | |
| 1-317 | Me, iPen | H, H | 5-F | H | |
| 1-318 | Me, iPen | H, H | 6-F | H | |
| 1-319 | Me, iPen | H, H | 7-F | H | |
| 1-320 | Me, iPen | H, H | 5-Cl | H | |
| 1-321 | Me, iPen | H, H | 6-Cl | H | |
| 1-322 | Me, iPen | H, H | 7-Cl | H | |

TABLE 1-continued

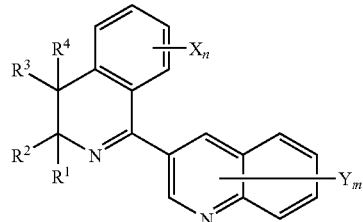

(Ia)

| Compound No. | R1, R2 | R3, R4 | Xn | Ym | Type of salt |
|---|---|---|---|---|---|
| 1-323 | Me, iPen | H, H | 5-Br | H | |
| 1-324 | Me, iPen | H, H | 6-Br | H | |
| 1-325 | Me, iPen | H, H | 7-Br | H | |
| 1-326 | Me, iPen | H, H | 5-I | H | |
| 1-327 | Me, iPen | H, H | 5-Me | H | |
| 1-328 | Me, iPen | H, H | 5-Vinyl | H | |
| 1-329 | Me, iPen | H, H | 5-Etynyl | H | |
| 1-330 | Me, iPen | H, H | 5-Ph | H | |
| 1-331 | Me, iPen | H, H | 5-FUR | H | |
| 1-332 | Me, iPen | H, H | 5-2THI | H | |
| 1-333 | Me, iPen | H, H | 5-3THI | H | |
| 1-334 | Me, iPen | H, H | 5-(2-Cl-2THI) | H | |
| 1-335 | Me, iPen | H, H | OXA | H | |
| 1-336 | Me, iPen | H, H | 5-MeMeIMD | H | |
| 1-337 | Me, iPen | H, H | 5-MeEtIMD | H | |
| 1-338 | Me, iPen | H, H | 5-EtEtIMD | H | |
| 1-339 | Me, iPen | H, H | 5-AllylEtIMD | H | |
| 1-340 | Me, iPen | H, H | 5-BnEtIMD | H | |
| 1-341 | Me, iPen | H, H | 5-PhEtIMD | H | |
| 1-342 | Me, iPen | H, H | 5-CN | H | |
| 1-343 | Me, iPen | H, H | 5,6-F2 | H | |
| 1-344 | Me, iPen | H, H | 5,6-Cl2 | H | |
| 1-345 | Et, Et | H, H | H | H | |
| 1-346 | Et, Et | H, H | H | 4-F | |
| 1-347 | Et, Et | H, H | H | 8-F | |
| 1-348 | Et, Et | H, H | H | 4-Cl | |
| 1-349 | Et, Et | H, H | H | 6-Cl | |
| 1-350 | Et, Et | H, H | H | 8-Cl | |
| 1-351 | Et, Et | H, H | H | 4-Me | |
| 1-352 | Et, Et | H, H | H | 8-Me | |
| 1-353 | Et, Et | H, H | H | 8-MeO | |
| 1-354 | Et, Et | H, H | H | 8-OH | |
| 1-355 | Et, Et | H, H | 5-F | H | |
| 1-356 | Et, Et | H, H | 6-F | H | |
| 1-357 | Et, Et | H, H | 7-F | H | |
| 1-358 | Et, Et | H, H | 5-Cl | H | |
| 1-359 | Et, Et | H, H | 6-Cl | H | |
| 1-360 | Et, Et | H, H | 7-Cl | H | |
| 1-361 | Et, Et | H, H | 5-Br | H | |
| 1-362 | Et, Et | H, H | 6-Br | H | |
| 1-363 | Et, Et | H, H | 7-Br | H | |
| 1-364 | Et, Et | H, H | 5-I | H | |
| 1-365 | Et, Et | H, H | 5-Me | H | |
| 1-366 | Et, Et | H, H | 5-Vinyl | H | |
| 1-367 | Et, Et | H, H | 5-Etynyl | H | |
| 1-368 | Et, Et | H, H | 5-Ph | H | |
| 1-369 | Et, Et | H, H | 5-FUR | H | |
| 1-370 | Et, Et | H, H | 5-2THI | H | |
| 1-371 | Et, Et | H, H | 5-3THI | H | |
| 1-372 | Et, Et | H, H | 5-(2-Cl-2THI) | H | |
| 1-373 | Et, Et | H, H | OXA | H | |
| 1-374 | Et, Et | H, H | 5-MeMeIMD | H | |
| 1-375 | Et, Et | H, H | 5-MeEtIMD | H | |
| 1-376 | Et, Et | H, H | 5-EtEtIMD | H | |
| 1-377 | Et, Et | H, H | 5-AllylEtIMID | H | |
| 1-378 | Et, Et | H, H | 5-BnEtIMD | H | |
| 1-379 | Et, Et | H, H | 5-PhEtIMD | H | |
| 1-380 | Et, Et | H, H | 5-CN | H | |
| 1-381 | Et, Et | H, H | 5,6-F2 | H | |
| 1-382 | Et, Et | H, H | 5,6-Cl2 | H | |
| 1-383 | Et, iBu | H, H | H | H | |
| 1-384 | Pr, Pr | H, H | H | H | |
| 1-385 | Me, ClCH2 | H, H | H | H | |
| 1-386 | Me, Cl2CH | H, H | H | H | |

TABLE 1-continued

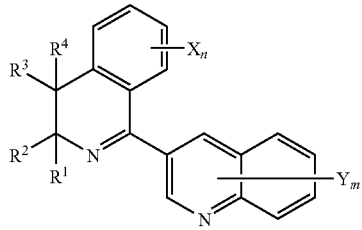

(Ia)

| Compound No. | R1, R2 | R3, R4 | Xn | Ym | Type of salt |
|---|---|---|---|---|---|
| 1-387 | Me, CF3 | H, H | H | H | |
| 1-388 | Me, CF3 | H, H | H | 4-F | |
| 1-389 | Me, CF3 | H, H | H | 8-F | |
| 1-390 | Me, CF3 | H, H | H | 4-Cl | |
| 1-391 | Me, CF3 | H, H | H | 6-Cl | |
| 1-392 | Me, CF3 | H, H | H | 8-Cl | |
| 1-393 | Me, CF3 | H, H | H | 4-Me | |
| 1-394 | Me, CF3 | H, H | H | 8-Me | |
| 1-395 | Me, CF3 | H, H | H | 8-MeO | |
| 1-396 | Me, CF3 | H, H | H | 8-OH | |
| 1-397 | Me, CF3 | H, H | 5-F | H | |
| 1-398 | Me, CF3 | H, H | 6-F | H | |
| 1-399 | Me, CF3 | H, H | 7-F | H | |
| 1-400 | Me, CF3 | H, H | 5-Cl | H | |
| 1-401 | Me, CF3 | H, H | 6-Cl | H | |
| 1-402 | Me, CF3 | H, H | 7-Cl | H | |
| 1-403 | Me, CF3 | H, H | 5-Br | H | |
| 1-404 | Me, CF3 | H, H | 6-Br | H | |
| 1-405 | Me, CF3 | H, H | 7-Br | H | |
| 1-406 | Me, CF3 | H, H | 5-I | H | |
| 1-407 | Me, CF3 | H, H | 5-Me | H | |
| 1-408 | Me, CF3 | H, H | 5-Vinyl | H | |
| 1-409 | Me, CF3 | H, H | 5-Etynyl | H | |
| 1-410 | Me, CF3 | H, H | 5-Ph | H | |
| 1-411 | Me, CF3 | H, H | 5-FUR | H | |
| 1-412 | Me, CF3 | H, H | 5-2THI | H | |
| 1-413 | Me, CF3 | H, H | 5-3THI | H | |
| 1-414 | Me, CF3 | H, H | 5-(2-Cl-2THI) | H | |
| 1-415 | Me, CF3 | H, H | OXA | H | |
| 1-416 | Me, CF3 | H, H | 5-MeMeIMD | H | |
| 1-417 | Me, CF3 | H, H | 5-MeEtIMD | H | |
| 1-418 | Me, CF3 | H, H | 5-EtEtIMD | H | |
| 1-419 | Me, CF3 | H, H | 5-AllylEtIMD | H | |
| 1-420 | Me, CF3 | H, H | 5-BnEtIMD | H | |
| 1-421 | Me, CF3 | H, H | 5-PhEtIMD | H | |
| 1-422 | Me, CF3 | H, H | 5-CN | H | |
| 1-423 | Me, CF3 | H, H | 5,6-F2 | H | |
| 1-424 | Me, CF3 | H, H | 5,6-Cl2 | H | |
| 1-425 | Me, CF3CH2 | H, H | H | H | |
| 1-426 | Me, CF3CH2 | H, H | H | 4-F | |
| 1-427 | Me, CF3CH2 | H, H | H | 8-F | |
| 1-428 | Me, CF3CH2 | H, H | H | 4-Cl | |
| 1-429 | Me, CF3CH2 | H, H | H | 6-Cl | |
| 1-430 | Me, CF3CH2 | H, H | H | 8-Cl | |
| 1-431 | Me, CF3CH2 | H, H | H | 4-Me | |
| 1-432 | Me, CF3CH2 | H, H | H | 8-Me | |
| 1-433 | Me, CF3CH2 | H, H | H | 8-MeO | |
| 1-434 | Me, CF3CH2 | H, H | H | 8-OH | |
| 1-435 | Me, CF3CH2 | H, H | 5-F | H | |
| 1-436 | Me, CF3CH2 | H, H | 6-F | H | |
| 1-437 | Me, CF3CH2 | H, H | 7-F | H | |
| 1-438 | Me, CF3CH2 | H, H | 5-Cl | H | |
| 1-439 | Me, CF3CH2 | H, H | 6-Cl | H | |
| 1-440 | Me, CF3CH2 | H, H | 7-Cl | H | |
| 1-441 | Me, CF3CH2 | H, H | 5-Br | H | |
| 1-442 | Me, CF3CH2 | H, H | 6-Br | H | |
| 1-443 | Me, CF3CH2 | H, H | 7-Br | H | |
| 1-444 | Me, CF3CH2 | H, H | 5-I | H | |
| 1-445 | Me, CF3CH2 | H, H | 5-Me | H | |
| 1-446 | Me, CF3CH2 | H, H | 5-Vinyl | H | |
| 1-447 | Me, CF3CH2 | H, H | 5-Etynyl | H | |
| 1-448 | Me, CF3CH2 | H, H | 5-Ph | H | |
| 1-449 | Me, CF3CH2 | H, H | 5-FUR | H | |
| 1-450 | Me, CF3CH2 | H, H | 5-2THI | H | |

TABLE 1-continued

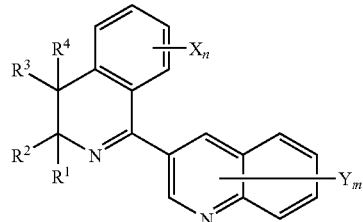
(Ia)

| Compound No. | R1, R2 | R3, R4 | Xn | Ym | Type of salt |
|---|---|---|---|---|---|
| 1-451 | Me, CF3CH2 | H, H | 5-3THI | H | |
| 1-452 | Me, CF3CH2 | H, H | 5-(2-Cl-2THI) | H | |
| 1-453 | Me, CF3CH2 | H, H | OXA | H | |
| 1-454 | Me, CF3CH2 | H, H | 5-MeMeIMD | H | |
| 1-455 | Me, CF3CH2 | H, H | 5-MeEtIMD | H | |
| 1-456 | Me, CF3CH2 | H, H | 5-EtEtIMD | H | |
| 1-457 | Me, CF3CH2 | H, H | 5-AllylEtIMD | H | |
| 1-458 | Me, CF3CH2 | H, H | 5-BnEtIMD | H | |
| 1-459 | Me, CF3CH2 | H, H | 5-PhEtIMD | H | |
| 1-460 | Me, CF3CH2 | H, H | 5-CN | H | |
| 1-461 | Me, CF3CH2 | H, H | 5,6-F2 | H | |
| 1-462 | Me, CF3CH2 | H, H | 5,6-Cl2 | H | |
| 1-463 | ClCH2, ClCH2 | H, H | H | H | |
| 1-464 | Me, Ph | H, H | H | H | |
| 1-465 | Me, Ph | H, H | H | 4-F | |
| 1-466 | Me, Ph | H, H | H | 8-F | |
| 1-467 | Me, Ph | H, H | H | 4-Cl | |
| 1-468 | Me, Ph | H, H | H | 6-Cl | |
| 1-469 | Me, Ph | H, H | H | 8-Cl | |
| 1-470 | Me, Ph | H, H | H | 4-Me | |
| 1-471 | Me, Ph | H, H | H | 8-Me | |
| 1-472 | Me, Ph | H, H | H | 8-MeO | |
| 1-473 | Me, Ph | H, H | H | 8-OH | |
| 1-474 | Me, Ph | H, H | 5-F | H | |
| 1-475 | Me, Ph | H, H | 6-F | H | |
| 1-476 | Me, Ph | H, H | 7-F | H | |
| 1-477 | Me, Ph | H, H | 5-Cl | H | |
| 1-478 | Me, Ph | H, H | 6-Cl | H | |
| 1-479 | Me, Ph | H, H | 7-Cl | H | |
| 1-480 | Me, Ph | H, H | 5-Br | H | |
| 1-481 | Me, Ph | H, H | 6-Br | H | |
| 1-482 | Me, Ph | H, H | 7-Br | H | |
| 1-483 | Me, Ph | H, H | 5-I | H | |
| 1-484 | Me, Ph | H, H | 5-Me | H | |
| 1-485 | Me, Ph | H, H | 5-Vinyl | H | |
| 1-486 | Me, Ph | H, H | 5-Etynyl | H | |
| 1-487 | Me, Ph | H, H | 5-Ph | H | |
| 1-488 | Me, Ph | H, H | 5-FUR | H | |
| 1-489 | Me, Ph | H, H | 5-2THI | H | |
| 1-490 | Me, Ph | H, H | 5-3THI | H | |
| 1-491 | Me, Ph | H, H | 5-(2-Cl-2THI) | H | |
| 1-492 | Me, Ph | H, H | OXA | H | |
| 1-493 | Me, Ph | H, H | 5-MeMeIMD | H | |
| 1-494 | Me, Ph | H, H | 5-MeEtIMD | H | |
| 1-495 | Me, Ph | H, H | 5-EtEtIMD | H | |
| 1-496 | Me, Ph | H, H | 5-AllylEtIMD | H | |
| 1-497 | Me, Ph | H, H | 5-BnEtIMD | H | |
| 1-498 | Me, Ph | H, H | 5-PhEtIMD | H | |
| 1-499 | Me, Ph | H, H | 5-CN | H | |
| 1-500 | Me, Ph | H, H | 5,6-F2 | H | |
| 1-501 | Me, Ph | H, H | 5,6-Cl2 | H | |
| 1-502 | Me, 4FPh | H, H | H | H | |
| 1-503 | Me, 4FPh | H, H | H | 4-F | |
| 1-504 | Me, 4FPh | H, H | H | 8-F | |
| 1-505 | Me, 4FPh | H, H | H | 4-Cl | |
| 1-506 | Me, 4FPh | H, H | H | 6-Cl | |
| 1-507 | Me, 4FPh | H, H | H | 8-Cl | |
| 1-508 | Me, 4FPh | H, H | H | 4-Me | |
| 1-509 | Me, 4FPh | H, H | H | 8-Me | |
| 1-510 | Me, 4FPh | H, H | H | 8-MeO | |
| 1-511 | Me, 4FPh | H, H | H | 8-OH | |
| 1-512 | Me, 4FPh | H, H | 5-F | H | |
| 1-513 | Me, 4FPh | H, H | 6-F | H | |
| 1-514 | Me, 4FPh | H, H | 7-F | H | |

TABLE 1-continued

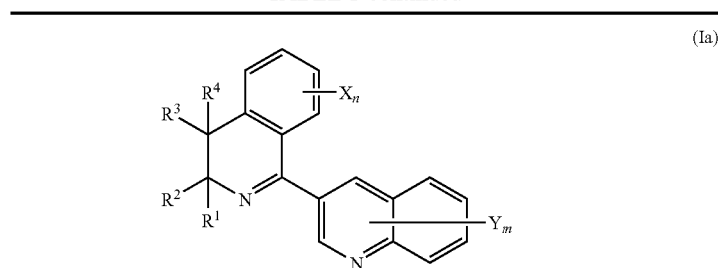
(Ia)

| Compound No. | R1, R2 | R3, R4 | Xn | Ym | Type of salt |
|---|---|---|---|---|---|
| 1-515 | Me, 4FPh | H, H | 5-Cl | H | |
| 1-516 | Me, 4FPh | H, H | 6-Cl | H | |
| 1-517 | Me, 4FPh | H, H | 7-Cl | H | |
| 1-518 | Me, 4FPh | H, H | 5-Br | H | |
| 1-519 | Me, 4FPh | H, H | 6-Br | H | |
| 1-520 | Me, 4FPh | H, H | 7-Br | H | |
| 1-521 | Me, 4FPh | H, H | 5-I | H | |
| 1-522 | Me, 4FPh | H, H | 5-Me | H | |
| 1-523 | Me, 4FPh | H, H | 5-Vinyl | H | |
| 1-524 | Me, 4FPh | H, H | 5-Etynyl | H | |
| 1-525 | Me, 4FPh | H, H | 5-Ph | H | |
| 1-526 | Me, 4FPh | H, H | 5-FUR | H | |
| 1-527 | Me, 4FPh | H, H | 5-2THI | H | |
| 1-528 | Me, 4FPh | H, H | 5-3THI | H | |
| 1-529 | Me, 4FPh | H, H | 5-(2-Cl-2THI) | H | |
| 1-530 | Me, 4FPh | H, H | OXA | H | |
| 1-531 | Me, 4FPl | H, H | 5-MeMeIMD | H | |
| 1-532 | Me, 4FPh | H, H | 5-MeEtIMD | H | |
| 1-533 | Me, 4FPh | H, H | 5-EtEtTMD | H | |
| 1-534 | Me, 4FPh | H, H | 5-AllylEtIMD | H | |
| 1-535 | Me, 4FPh | H, H | 5-BnEtIMD | H | |
| 1-536 | Me, 4FPh | H, H | 5-PhEtIMD | H | |
| 1-537 | Me, 4FPh | H, H | 5-CN | H | |
| 1-538 | Me, 4FPh | H, H | 5,6-F2 | H | |
| 1-539 | Me, 4FPh | H, H | 5,6-Cl2 | H | |
| 1-540 | Me, 4ClPh | H, H | H | H | |
| 1-541 | Me, 4ClPh | H, H | H | 4-F | |
| 1-542 | Me, 4ClPh | H, H | H | 8-F | |
| 1-543 | Me, 4ClPh | H, H | H | 4-Cl | |
| 1-544 | Me, 4ClPh | H, H | H | 6-Cl | |
| 1-545 | Me, 4ClPh | H, H | H | 8-Cl | |
| 1-546 | Me, 4ClPh | H, H | H | 4-Me | |
| 1-547 | Me, 4ClPh | H, H | H | 8-Me | |
| 1-548 | Me, 4ClPh | H, H | H | 8-MeO | |
| 1-549 | Me, 4ClPh | H, H | H | 8-OH | |
| 1-550 | Me, 4ClPh | H, H | 5-F | H | |
| 1-551 | Me, 4ClPh | H, H | 6-F | H | |
| 1-552 | Me, 4ClPh | H, H | 7-F | H | |
| 1-553 | Me, 4ClPh | H, H | 5-Cl | H | |
| 1-554 | Me, 4ClPh | H, H | 6-Cl | H | |
| 1-555 | Me, 4ClPh | H, H | 7-Cl | H | |
| 1-556 | Me, 4ClPh | H, H | 5-Br | H | |
| 1-557 | Me, 4ClPh | H, H | 6-Br | H | |
| 1-558 | Me, 4ClPh | H, H | 7-Br | H | |
| 1-559 | Me, 4ClPh | H, H | 5-I | H | |
| 1-560 | Me, 4ClPh | H, H | 5-Me | H | |
| 1-561 | Me, 4ClPh | H, H | 5-Vinyl | H | |
| 1-562 | Me, 4ClPh | H, H | 5-Etynyl | H | |
| 1-563 | Me, 4ClPh | H, H | 5-Ph | H | |
| 1-564 | Me, 4ClPh | H, H | 5-FUR | H | |
| 1-565 | Me, 4ClPh | H, H | 5-2THI | H | |
| 1-566 | Me, 4ClPh | H, H | 5-3THI | H | |
| 1-567 | Me, 4ClPh | H, H | 5(2-Cl-2THI) | H | |
| 1-568 | Me, 4ClPh | H, H | OXA | H | |
| 1-569 | Me, 4ClPh | H, H | 5-MeMeIMD | H | |
| 1-570 | Me, 4ClPh | H, H | 5-MeEtIMD | H | |
| 1-571 | Me, 4ClPh | H, H | 5-EtEtIMD | H | |
| 1-572 | Me, 4ClPh | H, H | 5-AllylEtIMD | H | |
| 1-573 | Me, 4ClPh | H, H | 5-BnEtIMD | H | |
| 1-574 | Me, 4ClPh | H, H | 5-PhEtIMD | H | |
| 1-575 | Me, 4ClPh | H, H | 5-CN | H | |
| 1-576 | Me, 4ClPh | H, H | 5,6-F2 | H | |
| 1-577 | Me, 4ClPh | H, H | 5,6-Cl2 | H | |
| 1-578 | Ph, CF3 | H, H | H | H | |

TABLE 1-continued

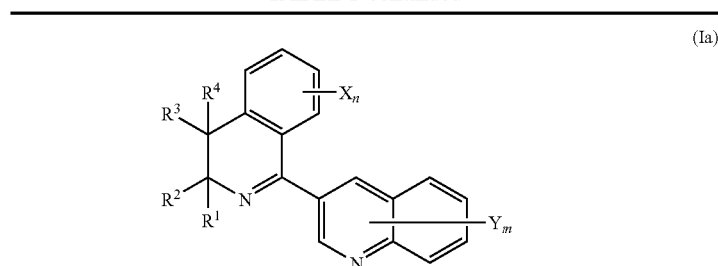

(Ia)

| Compound No. | R1, R2 | R3, R4 | Xn | Ym | Type of salt |
|---|---|---|---|---|---|
| 1-579 | Ph, CF3 | H, H | 5-F | H | |
| 1-580 | Ph, CF3 | H, H | 5-Cl | H | |
| 1-581 | Ph, CF3 | H, H | 5-Br | H | |
| 1-582 | Ph, CF3 | H, H | 5-I | H | |
| 1-583 | Ph, CF3 | H, H | 5-Me | H | |
| 1-584 | Ph, CF3 | H, H | 5-Vinyl | H | |
| 1-585 | Ph, CF3 | H, H | 5-Etynyl | H | |
| 1-586 | Ph, CF3 | H, H | 5-Ph | H | |
| 1-587 | Ph, CF3 | H, H | 5-FUR | H | |
| 1-588 | Ph, CF3 | H, H | 5-2THI | H | |
| 1-589 | Ph, CF3 | H, H | 5-3THI | H | |
| 1-590 | Ph, CF3 | H, H | 5-MeEtIMD | H | |
| 1-591 | Ph, CF3 | H, H | 5-EtEtIMD | H | |
| 1-592 | Ph, CF3 | H, H | 5-PhEtIMD | H | |
| 1-593 | Ph, CF3 | H, H | 5-CN | H | |
| 1-594 | ClCH2, 4FPh | H, H | H | H | |
| 1-595 | ClCH2, 4FPh | H, H | H | 4-F | |
| 1-596 | ClCH2, 4FPh | H, H | H | 8-F | |
| 1-597 | ClCH2, 4FPh | H, H | H | 4-Cl | |
| 1-598 | ClCH2, 4FPh | H, H | H | 6-Cl | |
| 1-599 | ClCH2, 4FPh | H, H | H | 8-Cl | |
| 1-600 | ClCH2, 4FPh | H, H | H | 4-Me | |
| 1-601 | ClCH2, 4FPh | H, H | H | 8-Me | |
| 1-602 | ClCH2, 4FPh | H, H | H | 8-MeO | |
| 1-603 | ClCH2, 4FPh | H, H | H | 8-OH | |
| 1-604 | ClCH2, 4FPh | H, H | 5-F | H | |
| 1-605 | ClCH2, 4FPh | H, H | 6-F | H | |
| 1-606 | ClCH2, 4FPh | H, H | 7-F | H | |
| 1-607 | ClCH2, 4FPh | H, H | 5-Cl | H | |
| 1-608 | ClCH2, 4FPh | H, H | 6-Cl | H | |
| 1-609 | ClCH2, 4FPh | H, H | 7-Cl | H | |
| 1-610 | ClCH2, 4FPh | H, H | 5-Br | H | |
| 1-611 | ClCH2, 4FPh | H, H | 6-Br | H | |
| 1-612 | ClCH2, 4FPh | H, H | 7-Br | H | |
| 1-613 | ClCH2, 4FPh | H, H | 5-I | H | |
| 1-614 | ClCH2, 4FPh | H, H | 5-Me | H | |
| 1-615 | ClCH2, 4FPh | H, H | 5-Vinyl | H | |
| 1-616 | ClCH2, 4FPh | H, H | 5-Etynyl | H | |
| 1-617 | ClCH2, 4FPh | H, H | 5-Ph | H | |
| 1-618 | ClCH2, 4FPh | H, H | 5-FUR | H | |
| 1-619 | ClCH2, 4FPh | H, H | 5-2THI | H | |
| 1-620 | ClCH2, 4FPh | H, H | 5-3THI | H | |
| 1-621 | ClCH2, 4FPh | H, H | 5-(2-Cl-2THI) | H | |
| 1-622 | ClCH2, 4FPh | H, H | OXA | H | |
| 1-623 | ClCH2, 4FPh | H, H | 5-MeMeIMD | H | |
| 1-624 | ClCH2, 4FPh | H, H | 5-MeEtIMD | H | |
| 1-625 | ClCH2, 4FPh | H, H | 5-EtEtIMD | H | |
| 1-626 | ClCH2, 4FPh | H, H | 5-AllylEtIMD | H | |
| 1-627 | ClCH2, 4FPh | H, H | 5-BnEtIMD | H | |
| 1-628 | ClCH2, 4FPh | H, H | 5-PhEtIMD | H | |
| 1-629 | ClCH2, 4FPh | H, H | 5-CN | H | |
| 1-630 | ClCH2, 4FPh | H, H | 5,6-F2 | H | |
| 1-631 | ClCH2, 4FPh | H, H | 5,6-Cl2 | H | |
| 1-632 | ClCH2, 4ClPh | H, H | H | H | |
| 1-633 | ClCH2, 4ClPh | H, H | H | 4-F | |
| 1-634 | ClCH2, 4ClPh | H, H | H | 8-F | |
| 1-635 | ClCH2, 4ClPh | H, H | H | 4-Cl | |
| 1-636 | ClCH2, 4ClPh | H, H | H | 6-Cl | |
| 1-637 | ClCH2, 4ClPh | H, H | H | 8-Cl | |
| 1-638 | ClCH2, 4ClPh | H, H | H | 4-Me | |
| 1-639 | ClCH2, 4ClPh | H, H | H | 8-Me | |
| 1-640 | ClCH2, 4ClPh | H, H | H | 8-MeO | |
| 1-641 | ClCH2, 4ClPh | H, H | H | 8-OH | |
| 1-642 | ClCH2, 4ClPh | H, H | 5-F | H | |

TABLE 1-continued

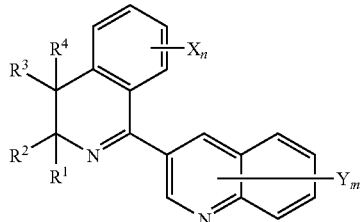

(Ia)

| Compound No. | R1, R2 | R3, R4 | Xn | Ym | Type of salt |
|---|---|---|---|---|---|
| 1-643 | ClCH2, 4ClPh | H, H | 6-F | H | |
| 1-644 | ClCH2, 4ClPh | H, H | 7-F | H | |
| 1-645 | ClCH2, 4ClPh | H, H | 5-Cl | H | |
| 1-646 | ClCH2, 4ClPh | H, H | 6-Cl | H | |
| 1-647 | ClCH2, 4ClPh | H, H | 7-Cl | H | |
| 1-648 | ClCH2, 4ClPh | H, H | 5-Br | H | |
| 1-649 | ClCH2, 4ClPh | H, H | 6-Br | H | |
| 1-650 | ClCH2, 4ClPh | H, H | 7-Br | H | |
| 1-651 | ClCH2, 4ClPh | H, H | 5-I | H | |
| 1-652 | ClCH2, 4ClPh | H, H | 5-Me | H | |
| 1-653 | ClCH2, 4ClPh | H, H | 5-Vinyl | H | |
| 1-654 | ClCH2, 4ClPh | H, H | 5-Etynyl | H | |
| 1-655 | ClCH2, 4ClPh | H, H | 5-Ph | H | |
| 1-656 | ClCH2, 4ClPh | H, H | 5-FUR | H | |
| 1-657 | ClCH2, 4ClPh | H, H | 5-2THI | H | |
| 1-658 | ClCH2, 4ClPh | H, H | 5-3THI | H | |
| 1-659 | ClCH2, 4ClPh | H, H | 5-(2-Cl-2THI) | H | |
| 1-660 | ClCH2, 4ClPh | H, H | OXA | H | |
| 1-661 | ClCH2, 4ClPh | H, H | 5-MeMeIMD | H | |
| 1-662 | ClCH2, 4ClPh | H, H | 5-MeEtIMD | H | |
| 1-663 | ClCH2, 4ClPh | H, H | 5-EtEtIMD | H | |
| 1-664 | ClCH2, 4ClPh | H, H | 5-AllylEtIMD | H | |
| 1-665 | ClCH2, 4ClPh | H, H | 5-BnEtIMD | H | |
| 1-666 | ClCH2, 4ClPh | H, H | 5-PhEtIMD | H | |
| 1-667 | ClCH2, 4ClPh | H, H | 5-CN | H | |
| 1-668 | ClCH2, 4ClPh | H, H | 5,6-F2 | H | |
| 1-669 | ClCH2, 4ClPh | H, H | 5,6-Cl2 | H | |
| 1-670 | Me, 3PYD | H, H | H | H | |
| 1-671 | Me, 4PYD | H, H | H | H | |
| 1-672 | Me, Bn | H, H | H | H | |
| 1-673 | Me, Bn | H, H | H | 4-F | |
| 1-674 | Me, Bn | H, H | H | 8-F | |
| 1-675 | Me, Bn | H, H | H | 4-Cl | |
| 1-676 | Me, Bn | H, H | H | 6-Cl | |
| 1-677 | Me, Bn | H, H | H | 8-Cl | |
| 1-678 | Me, Bn | H, H | H | 4-Me | |
| 1-679 | Me, Bn | H, H | H | 8-Me | |
| 1-680 | Me, Bn | H, H | H | 8-MeO | |
| 1-681 | Me, Bn | H, H | H | 8-OH | |
| 1-682 | Me, Bn | H, H | 5-F | H | |
| 1-683 | Me, Bn | H, H | 6-F | H | |
| 1-684 | Me, Bn | H, H | 7-F | H | |
| 1-685 | Me, Bn | H, H | 5-Cl | H | |
| 1-686 | Me, Bn | H, H | 6-Cl | H | |
| 1-687 | Me, Bn | H, H | 7-Cl | H | |
| 1-688 | Me, Bn | H, H | 5-Br | H | |
| 1-689 | Me, Bn | H, H | 6-Br | H | |
| 1-690 | Me, Bn | H, H | 7-Br | H | |
| 1-691 | Me, Bn | H, H | 5-I | H | |
| 1-692 | Me, Bn | H, H | 5-Me | H | |
| 1-693 | Me, Bn | H, H | 5-Vinyl | H | |
| 1-694 | Me, Bn | H, H | 5-Etynyl | H | |
| 1-695 | Me, Bn | H, H | 5-Ph | H | |
| 1-696 | Me, Bn | H, H | 5-FUR | H | |
| 1-697 | Me, Bn | H, H | 5-2THI | H | |
| 1-698 | Me, Bn | H, H | 5-3THI | H | |
| 1-699 | Me, Bn | H, H | 5-(2-Cl-2THI) | H | |
| 1-700 | Me, Bn | H, H | OXA | H | |
| 1-701 | Me, Bn | H, H | 5-MeMeIMD | H | |
| 1-702 | Me, Bn | H, H | 5-MeEtIMD | H | |
| 1-703 | Me, Bn | H, H | 5-EtEtIMD | H | |
| 1-704 | Me, Bn | H, H | 5-AllylEtIMD | H | |
| 1-705 | Me, Bn | H, H | 5-BnEtIMD | H | |
| 1-706 | Me, Bn | H, H | 5-PhEtIMD | H | |

TABLE 1-continued

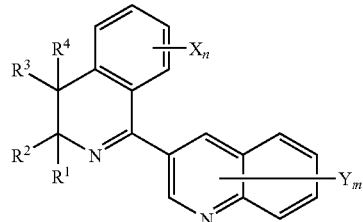

(Ia)

| Compound No. | R1, R2 | R3, R4 | Xn | Ym | Type of salt |
|---|---|---|---|---|---|
| 1-707 | Me, Bn | H, H | 5-CN | H | |
| 1-708 | Me, Bn | H, H | 5,6-F2 | H | |
| 1-709 | Me, Bn | H, H | 5,6-Cl2 | H | |
| 1-710 | cPen | H, H | H | H | |
| 1-711 | cPen | H, H | H | 4-F | |
| 1-712 | cPen | H, H | H | 8-F | |
| 1-713 | cPen | H, H | H | 4-Cl | |
| 1-714 | cPen | H, H | H | 6-Cl | |
| 1-715 | cPen | H, H | H | 8-Cl | |
| 1-716 | cPen | H, H | H | 4-Me | |
| 1-717 | cPen | H, H | H | 8-Me | |
| 1-718 | cPen | H, H | H | 8-MoO | |
| 1-719 | cPen | H, H | H | 8-OH | |
| 1-720 | cPen | H, H | 5-F | H | |
| 1-721 | cPen | H, H | 6-F | H | |
| 1-722 | cPen | H, H | 7-F | H | |
| 1-723 | cPen | H, H | 6-F | 4-Me | |
| 1-724 | cPen | H, H | 5-Cl | H | |
| 1-725 | cPen | H, H | 6-Cl | H | |
| 1-726 | cPen | H, H | 7-Cl | H | |
| 1-727 | cPen | H, H | 5-Br | H | |
| 1-728 | cPen | H, H | 6-Br | H | |
| 1-729 | cPen | H, H | 7-Br | H | |
| 1-730 | cPen | H, H | 5-I | H | |
| 1-731 | cPen | H, H | 5-Me | H | |
| 1-732 | cPen | H, H | 5-Vinyl | H | |
| 1-733 | cPen | H, H | 5-Etynyl | H | |
| 1-734 | cPen | H, H | 5-Ph | H | |
| 1-735 | cPen | H, H | 5-FUR | H | |
| 1-736 | cPen | H, H | 5-2THI | H | |
| 1-737 | cPen | H, H | 5-3THI | H | |
| 1-738 | cPen | H, H | 5-(2-Cl-2THI) | H | |
| 1-739 | cPen | H, H | OXA | H | |
| 1-740 | cPen | H, H | 5-MeMeIMD | H | |
| 1-741 | cPen | H, H | 5-MeEtIMD | H | |
| 1-742 | cPen | H, H | 5-EtEtIMD | H | |
| 1-743 | cPen | H, H | 5-AllylEtIMD | H | |
| 1-744 | cPen | H, H | 5-BnEtIMD | H | |
| 1-745 | cPen | H, H | 5-PhEtIMD | H | |
| 1-746 | cPen | H, H | 5-CN | H | |
| 1-747 | cPen | H, H | 5,6-F2 | H | |
| 1-748 | cPen | H, H | 5,6-Cl2 | H | |
| 1-749 | cHex | H, H | H | H | |
| 1-750 | cHex | H, H | H | 4-F | |
| 1-751 | cHex | H, H | H | 8-F | |
| 1-752 | cHex | H, H | H | 4-Cl | |
| 1-753 | cHex | H, H | H | 6-Cl | |
| 1-754 | cHex | H, H | H | 8-Cl | |
| 1-755 | cHex | H, H | H | 4-Me | |
| 1-756 | cHex | H, H | H | 8-Me | |
| 1-757 | cHex | H, H | H | 8-MeO | |
| 1-758 | cHex | H, H | H | 8-OH | |
| 1-759 | cHex | H, H | 5-F | H | |
| 1-760 | cHex | H, H | 6-F | H | |
| 1-761 | cHex | H, H | 7-F | H | |
| 1-762 | cHex | H, H | 5-F | 4-Me | |
| 1-763 | cHex | H, H | 5-Cl | H | |
| 1-764 | cHex | H, H | 6-Cl | H | |
| 1-765 | cHex | H, H | 7-Cl | H | |
| 1-766 | cHex | H, H | 5-Cl | 4-Me | |
| 1-767 | cHex | H, H | 5-Br | H | |
| 1-768 | cHex | H, H | 6-Br | H | |
| 1-769 | cHex | H, H | 7-Br | H | |
| 1-770 | cHex | H, H | 5-I | H | |

TABLE 1-continued

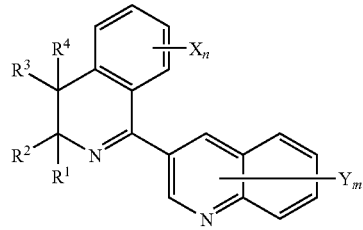

(Ia)

| Compound No. | R1, R2 | R3, R4 | Xn | Ym | Type of salt |
|---|---|---|---|---|---|
| 1-771 | cHex | H, H | 5-Me | H | |
| 1-772 | cHex | H, H | 6-Me | H | |
| 1-773 | cHex | H, H | 7-Me | H | |
| 1-774 | cHex | H, H | 6-Me | 4-Me | |
| 1-775 | cHex | H, H | 5-FUR | H | |
| 1-776 | cHex | H, H | 5-2THI | H | |
| 1-777 | cHex | H, H | 5-3THI | H | |
| 1-778 | cHex | H, H | 5-(2-Cl-2THI) | H | |
| 1-779 | cHex | H, H | OXA | H | |
| 1-780 | cHex | H, H | 5-MeMeIMD | H | |
| 1-781 | cHex | H, H | 5-MeEtIMD | H | |
| 1-782 | cHex | H, H | 5-EtEtIMD | H | |
| 1-783 | cHex | H, H | 5-AllylEtIMD | H | |
| 1-784 | cHex | H, H | 5-BnEtIMD | H | |
| 1-785 | cHex | H, H | 5-PhEtIMD | H | |
| 1-786 | cHex | H, H | 6-CN | H | |
| 1-787 | cHex | H, H | 5,6-F2 | H | |
| 1-788 | cHex | H, H | 5,6-Cl2 | H | |
| 1-789 | cHep | H, H | H | H | |
| 1-790 | 3-MecPen | H, H | H | H | |
| 1-791 | 3-MecPen | H, H | 5-F | H | |
| 1-792 | Me, Me | H, H | H | H | HCl salt |
| 1-793 | Me, Me | H, H | 5-F | H | HCl salt |
| 1-794 | Me, Me | H, H | 5-Cl | H | HCl salt |
| 1-795 | Me, Me | H, H | H | H | $H_2SO_4$ salt |
| 1-796 | Me, Me | H, H | 5-F | H | $H_2SO_4$ salt |
| 1-797 | Me, Me | H, H | 5-Cl | H | $H_2SO_4$ salt |
| 1-798 | Me, Me | H, H | H | H | $HNO_3$ salt |
| 1-799 | Me, Me | H, H | 5-F | H | $HNO_3$ salt |
| 1-800 | Me, Me | H, H | 5-Cl | H | $HNO_3$ salt |
| 1-801 | MeMe | H, H | H | H | $(COOH)_2$ salt |
| 1-802 | Me, Me | H, H | 5-F | H | $(COOH)_2$ salt |
| 1-803 | Me, Me | H, H | H | H | MsOH salt |
| 1-804 | Me, Me | H, H | 5-F | H | MsOH salt |
| 1-805 | Me, Me | H, H | H | H | Salicylate |
| 1-806 | Me, Me | H, H | 5-F | H | Salicylate |
| 1-807 | Me, Me | H, H | 5-F | H | fumarate |
| 1-808 | Me, Et | H, H | H | H | HCl salt |
| 1-809 | Me, Et | H, H | 5-F | H | HCl salt |
| 1-810 | Me, Et | H, H | 5-Cl | H | HCl salt |
| 1-811 | Me, Et | H, H | H | H | $H_2SO_4$ salt |
| 1-812 | Me, Et | H, H | 5-F | H | $H_2SO_4$ salt |
| 1-813 | Me, Et | H, H | 5-Cl | H | $H_2SO_4$ salt |
| 1-814 | Me, Et | H, H | H | H | $HNO_3$ salt |
| 1-815 | Me, Et | H, H | 5-F | H | $HNO_3$ salt |
| 1-816 | Me, Et | H, H | 5-Cl | H | $HNO_3$ salt |
| 1-817 | Me, Et | H, H | H | H | $(COOH)_2$ salt |
| 1-818 | Me, Et | H, H | 5-F | H | $(COOH)_2$ salt |
| 1-819 | Me, Et | H, H | H | H | MsOH salt |
| 1-820 | Me, Et | H, H | 5-F | H | MsOH salt |
| 1-821 | Me, Et | H, H | H | H | Salicylate |
| 1-822 | Me, Et | H, H | 5-F | H | Salicylate |
| 1-823 | Me, Et | H, H | 5-F | H | fumarate |
| 1-824 | Me, Pr | H, H | H | H | HCl salt |
| 1-825 | Me, Pr | H, H | 5-F | H | HCl salt |
| 1-826 | Me, Pr | H, H | 5-Cl | H | HCl salt |
| 1-827 | Me, Pr | H, H | H | H | $H_2SO_4$ salt |
| 1-828 | Me, Pr | H, H | 5-F | H | $H_2SO_4$ salt |
| 1-829 | Me, Pr | H, H | 5-Cl | H | $H_2SO_4$ salt |
| 1-830 | Me, Pr | H, H | H | H | $HNO_3$ salt |
| 1-831 | Me, Pr | H, H | 5-F | H | $HNO_3$ salt |
| 1-832 | Me, Pr | H, H | 5-Cl | H | $HNO_3$ salt |
| 1-833 | Me, Pr | H, H | H | H | $(COOH)_2$ salt |
| 1-834 | Me, Pr | H, H | 5-F | H | $(COOH)_2$ salt |

TABLE 1-continued

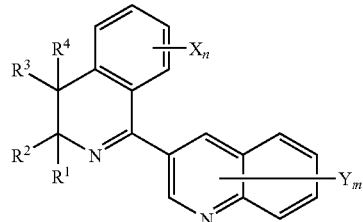
(Ia)

| Compound No. | R1, R2 | R3, R4 | Xn | Ym | Type of salt |
| --- | --- | --- | --- | --- | --- |
| 1-835 | Me, Pr | H, H | H | H | MsOH salt |
| 1-836 | Me, Pr | H, H | 5-F | H | MsOH salt |
| 1-837 | Me, Pr | H, H | H | H | Salicylate |
| 1-838 | Me, Pr | H, H | 5-F | H | Salicylate |
| 1-839 | Me, Pr | H, H | 5-F | H | fumarate |
| 1-840 | Me, Ph | H, H | H | H | HCl salt |
| 1-841 | Me, Ph | H, H | 5-F | H | HCl salt |
| 1-842 | Me, Ph | H, H | 5-Cl | H | HCl salt |
| 1-843 | Me, Ph | H, H | H | H | $H_2SO_4$ salt |
| 1-844 | Me, Ph | H, H | 5-F | H | $H_2SO_4$ salt |
| 1-845 | Me, Ph | H, H | 5-Cl | H | $H_2SO_4$ salt |
| 1-846 | Me, Ph | H, H | H | H | $HNO_3$ salt |
| 1-847 | Me, Ph | H, H | 5-F | H | $HNO_3$ salt |
| 1-848 | Me, Ph | H, H | 5-Cl | H | $HNO_3$ salt |
| 1-849 | Me, Ph | H, H | H | H | $(COOH)_2$ salt |
| 1-850 | Me, Ph | H, H | 5-F | H | $(COOH)_2$ salt |
| 1-851 | Me, Ph | H, H | H | H | MsOH salt |
| 1-852 | Me, Ph | H, H | 5-F | H | MsOH salt |
| 1-853 | Me, Ph | H, H | H | H | Salicylate |
| 1-854 | Me, Ph | H, H | 5-F | H | Salicylate |
| 1-855 | Me, Ph | H, H | 5-F | H | fumarate |
| 1-856 | Me, Me | H, Me | H | H | |
| 1-857 | Me, Me | H, Me | 5-F | H | |
| 1-858 | Me, Me | H, Me | 5-Cl | H | |
| 1-859 | Me, Me | H, Et | H | H | |
| 1-860 | Me, Me | H, Et | 5-F | H | |
| 1-861 | Me, Me | H, Et | 5-Cl | H | |
| 1-862 | Me, Me | H, Pr | H | H | |
| 1-863 | Me, Me | H, Pr | 5-F | H | |
| 1-864 | Me, Me | H, Pr | 5-Cl | H | |
| 1-865 | Me, Me | Me, Me | H | H | |
| 1-866 | Me, Me | Me, Me | 5-F | H | |
| 1-867 | Me, Me | Me, Me | 5-Cl | H | |
| 1-868 | Me, Et | H, Me | H | H | |
| 1-869 | Me, Et | H, Me | 5-F | H | |
| 1-870 | Me, Et | H, Me | 5-Cl | H | |
| 1-871 | Me, Pr | H, Me | H | H | |
| 1-872 | Me, Pr | H, Me | 5-F | H | |
| 1-873 | Me, Pr | H, Me | 5-Cl | H | |
| 1-874 | Me, Ph | H, Me | H | H | |
| 1-875 | Me, Ph | H, Me | 5-F | H | |
| 1-876 | Me, Ph | H, Me | 5-Cl | H | |
| 1-877 | Me, Ph | Me, Me | H | H | |
| 1-878 | Me, Ph | Me, Me | 5-F | H | |
| 1-879 | Me, Ph | Me, Me | 5-Cl | H | |
| 1-880 | Me, Me | H, H | 5-iPr | H | |
| 1-881 | Me, Me | H, H | 5-CH(Me)$CH_2CH_3$ | H | |
| 1-882 | Me, Me | H, H | 5-C(Me)=$CH_2$ | H | |
| 1-883 | Me, Me | H, H | 5-CH=CHCO$_2$Me | H | |
| 1-884 | Me, Me | H, H | 5-$CH_2$F | H | |
| 1-885 | Me, Me | H, H | 5-$CH_2$Cl | H | |
| 1-886 | Me, Me | H, H | 5-CHF$_2$ | H | |
| 1-887 | Me, Me | H, H | 5-$CH_2$OH | H | |
| 1-888 | Me, Me | H, H | 5-C(Me)$_2$OH | H | |
| 1-889 | Me, Me | H, H | 5-$CH_2$OMe | H | |
| 1-890 | Me, Me | H, H | 5-$CH_2CO_2$Me | H | |
| 1-891 | Me, Me | H, H | 5-NHCOPh | H | |
| 1-892 | Me, Me | H, H | 5-NHCO(2-FPh) | H | |
| 1-893 | Me, Me | H, H | 5-NHCO(3-FPh) | H | |
| 1-894 | Me, Me | H, H | 5-NHCO(4-FPh) | H | |
| 1-895 | Me, Me | H, H | 5-CO2H | H | |
| 1-896 | Me, Me | H, H | 5-CO2Me | H | |
| 1-897 | Me, Me | H, H | 5-CO2Et | H | |
| 1-898 | Me, Me | H, H | 5-CONH2 | H | |

TABLE 1-continued (Ia)

| Compound No. | R1, R2 | R3, R4 | Xn | Ym | Type of salt |
|---|---|---|---|---|---|
| 1-899 | Me, Me | H, H | 5-F | 2-Me | |
| 1-900 | Me, Me | H, H | 5-F | 4-Me | |
| 1-901 | Me, Me | H, Me | 5-F | 2-Me | |
| 1-902 | Me, Me | H, Me | 5-F | 8-Me | |
| 1-903 | Me, Me | H, Me | 5-F | 8-MeO | |
| 1-904 | Me, Me | Me, Me | 6-F | H | |
| 1-905 | Me, Me | Me, Me | 7-F | H | |
| 1-906 | Me, Me | Me, Me | 5-F | 2-Me | |
| 1-907 | Me, Me | Me, Me | 5-F | 4-Me | |
| 1-908 | Me, Me | Me, Me | 6-Cl | H | |
| 1-909 | Me, Me | Me, Me | 7-Cl | H | |
| 1-910 | Me, Me | Me, Me | 5-F | H | HCl salt |
| 1-911 | Me, Me | Me, Me | 5-F | H | $H_2SO_4$ salt |
| 1-912 | Me, Me | Me, Me | 5-F | H | $HNO_3$ salt |
| 1-913 | Me, Me | Me, Me | 5-F | H | MsOH salt |
| 1-914 | Me, Me | Me, Me | 5-Me | H | |
| 1-915 | Me, Me | Me, Me | 6-Me | H | |
| 1-916 | Me, Me | Me, Me | 7-Me | H | |
| 1-917 | Me, Me | Me, Me | 5-F | 6-F | |
| 1-918 | Me, Me | Me, Me | 5-F | 8-F | |
| 1-919 | Me, Me | Me, Me | 5-F | 8-Me | |
| 1-920 | Me, Me | Me, Me | 5-F | 8-MeO | |
| 1-921 | Me, Me | cPen | H | H | |
| 1-922 | cPen | Me, Me | H | H | |
| 1-923 | Me, Me | cHex | H | H | |
| 1-924 | cHex | Me, Me | H | H | |
| 1-925 | cBu | H, H | 5-F | H | |
| 1-926 | Me, Me | $CH_2=$ | 5-F | H | |
| 1-927 | Me, Me | H, F | 5-F | H | |
| 1-928 | Me, Me | H, Cl | 5-F | H | |
| 1-929 | Me, Me | F, F | H | H | |
| 1-930 | Me, Me | F, F | 5-F | H | |
| 1-931 | Me, Me | H, OH | 5-F | H | |
| 1-932 | Me, Me | H, OMe | 5-F | H | |
| 1-933 | Me, Me | O= | H | H | |
| 1-934 | Me, Me | O= | 5-F | H | |
| 1-935 | Me, Me | Me, OH | 5-F | H | |
| 1-936 | Me, Me | Et, OH | 5-F | H | |
| 1-937 | Me, Me | Me, OMe | 5-F | H | |
| 1-938 | Me, Me | Me, OEt | 5-F | H | |
| 1-939 | Me, Me | Et, OMe | 5-F | H | |
| 1-940 | Me, Me | F, F | 6-F | H | |
| 1-941 | Me, Me | F, F | 7-F | H | |
| 1-942 | Me, Me | F, F | 5-Cl | H | |
| 1-943 | Me, Me | F, F | 6-Cl | H | |
| 1-944 | Me, Me | F, F | 7-Cl | H | |
| 1-945 | Me, Me | F, F | 5-Br | H | |
| 1-946 | Me, Me | F, F | 6-Br | H | |
| 1-947 | Me, Me | F, F | 7-Br | H | |
| 1-948 | Me, Me | F, F | 5-Me | H | |
| 1-949 | Me, Me | F, F | 6-Me | H | |
| 1-950 | Me, Me | F, F | 6-MeO | H | |
| 1-951 | Me, Me | F, F | 5,7-$Cl_2$ | H | |
| 1-952 | Me, Me | F, F | 6-F,7-Me | H | |
| 1-953 | Me, Me | O= | 6-F | H | |
| 1-954 | Me, Me | O= | 7-F | H | |
| 1-955 | Me, Me | O= | 5-Cl | H | |
| 1-956 | Me, Me | O= | 6-Cl | H | |
| 1-957 | Me, Me | O= | 7-Cl | H | |
| 1-958 | Me, Me | O= | 5-Br | H | |
| 1-959 | Me, Me | O= | 6-Br | H | |
| 1-960 | Me, Me | O= | 7-Br | H | |

TABLE 2

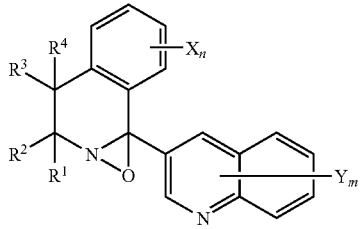

(Ib)

| Compound No. | R1, R2 | R3, R4 | Xn | Ym |
|---|---|---|---|---|
| 2-1 | Me, Me | H, H | H | H |
| 2-2 | Me, Me | H, H | H | 5-F |
| 2-3 | Me, Me | H, H | H | 6-F |
| 2-4 | Me, Me | H, H | H | 7-F |
| 2-5 | Me, Me | H, H | H | 8-F |
| 2-6 | Me, Me | H, H | H | 5-Cl |
| 2-7 | Me, Me | H, H | H | 6-Cl |
| 2-8 | Me, Me | H, H | H | 7-Cl |
| 2-9 | Me, Me | H, H | H | 8-Cl |
| 2-10 | Me, Me | H, H | H | 2-Me |
| 2-11 | Me, Me | H, H | H | 4-Me |
| 2-12 | Me, Me | H, H | H | 5-Me |
| 2-13 | Me, Me | H, H | H | 6-Me |
| 2-14 | Me, Me | H, H | H | 7-Me |
| 2-15 | Me, Me | H, H | H | 8-Me |
| 2-16 | Me, Me | H, H | H | 8-MeO |
| 2-17 | Me, Me | H, H | H | 2-OH |
| 2-18 | Me, Me | H, H | H | 4-OH |
| 2-19 | Me, Me | H, H | H | 8-OH |
| 2-20 | Me, Me | H, H | 5-F | H |
| 2-21 | Me, Me | H, H | 5-F | 5-F |
| 2-22 | Me, Me | H, H | 5-F | 6-F |
| 2-23 | Me, Me | H, H | 5-F | 7-F |
| 2-24 | Me, Me | H, H | 5-F | 8-F |
| 2-25 | Me, Me | H, H | 5-F | 5-Cl |
| 2-26 | Me, Me | H, H | 5-F | 6-Cl |
| 2-27 | Me, Me | H, H | 5-F | 7-Cl |
| 2-28 | Me, Me | H, H | 5-F | 8-Cl |
| 2-29 | Me, Me | H, H | 5-F | 2-Me |
| 2-30 | Me, Me | H, H | 5-F | 4-Me |
| 2-31 | Me, Me | H, H | 5-F | 5-Me |
| 2-32 | Me, Me | H, H | 5-F | 6-Me |
| 2-33 | Me, Me | H, H | 5-F | 7-Me |
| 2-34 | Me, Me | H, H | 5-F | 8-Me |
| 2-35 | Me, Me | H, H | 5-F | 8-MeO |
| 2-36 | Me, Me | H, H | 5-F | 2-OH |
| 2-37 | Me, Me | H, H | 5-F | 4-OH |
| 2-38 | Me, Me | H, H | 5-F | 1-OH |
| 2-39 | Me, Me | H, H | 6-F | H |
| 2-40 | Me, Me | H, H | 7-F | H |
| 2-41 | Me, Me | H, H | 8-F | H |
| 2-42 | Me, Me | H, H | 5-Cl | H |
| 2-43 | Me, Me | H, H | 6-Cl | H |
| 2-44 | Me, Me | H, H | 7-Cl | H |
| 2-45 | Me, Me | H, H | 7-Me | H |
| 2-46 | Me, Me | H, H | 8-Me | H |
| 2-47 | Me, Me | H, H | 5-Et | H |
| 2-48 | Me, Me | H, H | 5-MeO | H |
| 2-49 | Me, Me | H, H | 6-MeO | H |
| 2-50 | Me, Me | H, H | 7-MeO | H |
| 2-51 | Me, Me | H, H | 8-MeO | H |
| 2-52 | Me, Me | H, H | 5-EtO | H |
| 2-53 | Me, Me | H, H | 5,6-F$_2$ | H |
| 2-54 | Me, Me | H, H | 6-F, 7-Me | H |
| 2-55 | Me, Me | H, Me | H | H |
| 2-56 | Me, Me | H, Me | H | H |
| 2-57 | Me, Me | H, Me | H | 5-F |
| 2-58 | Me, Me | H, Me | H | 6-F |
| 2-59 | Me, Me | H, Me | H | 7-F |
| 2-60 | Me, Me | H, Me | H | 8-F |
| 2-61 | Me, Me | H, Me | H | 2-Me |
| 2-62 | Me, Me | H, Me | H | 4-Me |
| 2-63 | Me, Me | H, Me | H | 8-Me |
| 2-64 | Me, Me | H, Me | H | 8-MeO |
| 2-65 | Me, Me | H, Me | 5-F | H |
| 2-66 | Me, Me | H, Me | 5-F | 5-F |
| 2-67 | Me, Me | H, Me | 5-F | 6-F |
| 2-68 | Me, Me | H, Me | 5-F | 7-F |
| 2-69 | Me, Me | H, Me | 5-F | 8-F |
| 2-70 | Me, Me | H, Me | 5-F | 2-Me |
| 2-71 | Me, Me | H, Me | 5-F | 4-Me |
| 2-72 | Me, Me | H, Me | 5-F | 8-Me |
| 2-73 | Me, Me | H, Me | 5-F | 8-MeO |
| 2-74 | Me, Me | H, Me | 6-F | H |
| 2-75 | Me, Me | H, Me | 7-F | H |
| 2-76 | Me, Me | H, Me | 8-F | H |
| 2-77 | Me, Me | H, Me | 5-Cl | H |
| 2-78 | Me, Me | H, Me | 6-Cl | H |
| 2-79 | Me, Me | H, Me | 7-Cl | H |
| 2-80 | Me, Me | H, Me | 8-Cl | H |
| 2-81 | Me, Me | H, Me | 5-Me | H |
| 2-82 | Me, Me | H, Me | 6-Me | H |
| 2-83 | Me, Me | H, Me | 7-Me | H |
| 2-84 | Me, Me | H, Me | 8-Me | H |
| 2-85 | Me, Me | H, Me | 5-MeO | H |
| 2-86 | Me, Me | H, Me | 6-MeO | H |
| 2-87 | Me, Me | H, Me | 7-MeO | H |
| 2-88 | Me, Me | H, Me | 8-MeO | H |
| 2-89 | Me, Me | H, Me | 5,6-F$_2$ | H |
| 2-90 | Me, Me | H, Me | 6-F, 7-Me | H |
| 2-91 | Me, Me | Me, Me | H | H |
| 2-92 | Me, Me | Me, Me | H | 5-F |
| 2-93 | Me, Me | Me, Me | H | 6-F |
| 2-94 | Me, Me | Me, Me | H | 7-F |
| 2-95 | Me, Me | Me, Me | H | 8-F |
| 2-96 | Me, Me | Me, Me | H | 2-Me |
| 2-97 | Me, Me | Me, Me | H | 4-Me |
| 2-98 | Me, Me | Me, Me | H | 8-Me |
| 2-99 | Me, Me | Me, Me | H | 8-MeO |
| 2-100 | Me, Me | Me, Me | 5-F | H |
| 2-101 | Me, Me | Me, Me | 5-F | 5-F |
| 2-102 | Me, Me | Me, Me | 5-F | 6-F |
| 2-103 | Me, Me | Me, Me | 5-F | 7-F |
| 2-104 | Me, Me | Me, Me | 5-F | 8-F |
| 2-105 | Me, Me | Me, Me | 5-F | 2-Me |
| 2-106 | Me, Me | Me, Me | 5-F | 4-Me |
| 2-107 | Me, Me | Me, Me | 5-F | 8-Me |
| 2-108 | Me, Me | Me, Me | 5-F | 8-OH |
| 2-109 | Me, Me | Me, Me | 6-F | H |
| 2-110 | Me, Me | Me, Me | 7-F | H |
| 2-111 | Me, Me | Me, Me | 8-F | H |
| 2-112 | Me, Me | Me, Me | 5-Cl | H |
| 2-113 | Me, Me | Me, Me | 6-Cl | H |
| 2-114 | Me, Me | Me, Me | 7-Cl | H |
| 2-115 | Me, Me | Me, Me | 8-Cl | H |
| 2-116 | Me, Me | Me, Me | 5-Me | H |
| 2-117 | Me, Me | Me, Me | 6-Me | H |
| 2-118 | Me, Me | Me, Me | 7-Me | H |
| 2-119 | Me, Me | Me, Me | 8-Me | H |
| 2-120 | Me, Me | Me, Me | 5-MeO | H |
| 2-121 | Me, Me | Me, Me | 6-MeO | H |
| 2-122 | Me, Me | Me, Me | 7-MeO | H |
| 2-123 | Me, Me | Me, Me | 8-MeO | H |
| 2-124 | Me, Me | Me, Me | 5,6-F$_2$ | H |
| 2-125 | Me, Me | Me, Me | 6-F, 7-Me | H |
| 2-126 | Me, Me | cPen | H | H |
| 2-127 | cPen | Me, Me | H | H |
| 2-128 | Me, Me | cHex | H | H |

TABLE 2-continued (Ib)

Structure: R³, R⁴ on carbon; R¹, R² on carbon adjacent to N-O; isoquinoline fused with Xn; connected to quinoline with Ym substituent.

| Compound No. | R1, R2 | R3, R4 | Xn | Ym |
|---|---|---|---|---|
| 2-129 | cHex | Me, Me | H | H |
| 2-130 | Me, Et | H, H | 5-F | H |
| 2-131 | Me, Me | CH₂= | 5-F | H |
| 2-132 | Me, Me | H, F | 5-F | H |
| 2-133 | Me, Me | H, Cl | 5-F | H |
| 2-134 | Me, Me | F, F | H | H |
| 2-135 | Me, Me | F, F | 5-F | H |
| 2-136 | Me, Me | H, OH | 5-F | H |
| 2-137 | Me, Me | H, OMe | 5-F | H |
| 2-138 | Me, Me | O= | H | H |
| 2-139 | Me, Me | O= | 5-F | H |
| 2-140 | Me, Me | Me, OH | 5-F | H |
| 2-141 | Me, Me | Et, OH | 5-F | H |
| 2-142 | Me, Me | Me, OMe | 5-F | H |
| 2-143 | Me, Me | Me, OEt | 5-F | H |
| 2-144 | Me, Me | Et, OMe | 5-F | H |

TABLE 3

(Ic)

| Compound No. | R1, R2 | R3, R4 | Xn | Ym |
|---|---|---|---|---|
| 3-1 | Me, Me | H, H | H | H |
| 3-2 | Me, Me | H, H | H | 5-F |
| 3-3 | Me, Me | H, H | H | 6-F |
| 3-4 | Me, Me | H, H | H | 7-F |
| 3-5 | Me, Me | H, H | H | 8-F |
| 3-6 | Me, Me | H, H | H | 5-Cl |
| 3-7 | Me, Me | H, H | H | 6-Cl |
| 3-8 | Me, Me | H, H | H | 7-Cl |
| 3-9 | Me, Me | H, H | H | 8-Cl |
| 3-10 | Me, Me | H, H | H | 2-Me |
| 3-11 | Me, Me | H, H | H | 4-Me |
| 3-12 | Me, Me | H, H | H | 5-Me |
| 3-13 | Me, Me | H, H | H | 6-Me |
| 3-14 | Me, Me | H, H | H | 7-Me |
| 3-15 | Me, Me | H, H | H | 8-Me |
| 3-16 | Me, Me | H, H | H | 8-MeO |
| 3-17 | Me, Me | H, H | H | 2-OH |
| 3-18 | Me, Me | H, H | H | 4-OH |
| 3-19 | Me, Me | H, H | H | 8-OH |
| 3-20 | Me, Me | H, H | 5-F | H |
| 3-21 | Me, Me | H, H | 5-F | 5-F |
| 3-22 | Me, Me | H, H | 5-F | 6-F |
| 3-23 | Me, Me | H, H | 5-F | 7-F |
| 3-24 | Me, Me | H, H | 5-F | 8-F |
| 3-25 | Me, Me | H, H | 5-F | 5-Cl |
| 3-26 | Me, Me | H, H | 5-F | 6-Cl |
| 3-27 | Me, Me | H, H | 5-F | 7-Cl |

TABLE 3-continued (Ic)

| Compound No. | R1, R2 | R3, R4 | Xn | Ym |
|---|---|---|---|---|
| 3-28 | Me, Me | H, H | 5-F | 8-Cl |
| 3-29 | Me, Me | H, H | 5-F | 2-Me |
| 3-30 | Me, Me | H, H | 5-F | 4-Me |
| 3-31 | Me, Me | H, H | 5-F | 5-Me |
| 3-32 | Me, Me | H, H | 5-F | 6-Me |
| 3-33 | Me, Me | H, H | 5-F | 7-Me |
| 3-34 | Me, Me | H, H | 5-F | 8-Me |
| 3-35 | Me, Me | H, H | 5-F | 8-MeO |
| 3-36 | Me, Me | H, H | 5-F | 2-OH |
| 3-37 | Me, Me | H, H | 5-F | 4-OH |
| 3-38 | Me, Me | H, H | 5-F | 1-OH |
| 3-39 | Me, Me | H, H | 6-F | H |
| 3-40 | Me, Me | H, H | 7-F | H |
| 3-41 | Me, Me | H, H | 8-F | H |
| 3-42 | Me, Me | H, H | 5-Cl | H |
| 3-43 | Me, Me | H, H | 6-Cl | H |
| 3-44 | Me, Me | H, H | 7-Cl | H |
| 3-45 | Me, Me | H, H | 7-Me | H |
| 3-46 | Me, Me | H, H | 8-Me | H |
| 3-47 | Me, Me | H, H | 5-Et | H |
| 3-48 | Me, Me | H, H | 5-MeO | H |
| 3-49 | Me, Me | H, H | 6-MeO | H |
| 3-50 | Me, Me | H, H | 7-MeO | H |
| 3-51 | Me, Me | H, H | 8-MeO | H |
| 3-52 | Me, Me | H, H | 5-EtO | H |
| 3-53 | Me, Me | H, H | 5,6-F₂ | H |
| 3-54 | Me, Me | H, H | 6-F, 7-Me | H |
| 3-55 | Me, Me | H, H | H | H |
| 3-56 | Me, Me | H, Me | H | H |
| 3-57 | Me, Me | H, Me | H | 5-F |
| 3-58 | Me, Me | H, Me | H | 6-F |
| 3-59 | Me, Me | H, Me | H | 7-F |
| 3-60 | Me, Me | H, Me | H | 8-F |
| 3-61 | Me, Me | H, Me | H | 2-Me |
| 3-62 | Me, Me | H, Me | H | 4-Me |
| 3-63 | Me, Me | H, Me | H | 8-Me |
| 3-64 | Me, Me | H, Me | H | 8-MeO |
| 3-65 | Me, Me | H, Me | 5-F | H |
| 3-66 | Me, Me | H, Me | 5-F | 5-F |
| 3-67 | Me, Me | H, Me | 5-F | 6-F |
| 3-68 | Me, Me | H, Me | 5-F | 7-F |
| 3-69 | Me, Me | H, Me | 5-F | 8-F |
| 3-70 | Me, Me | H, Me | 5-F | 2-Me |
| 3-71 | Me, Me | H, Me | 5-F | 4-Me |
| 3-72 | Me, Me | H, Me | 5-F | 8-Me |
| 3-73 | Me, Me | H, Me | 5-F | 8-MeO |
| 3-74 | Me, Me | H, Me | 6-F | H |
| 3-75 | Me, Me | H, Me | 7-F | H |
| 3-76 | Me, Me | H, Me | 8-F | H |
| 3-77 | Me, Me | H, Me | 5-Cl | H |
| 3-78 | Me, Me | H, Me | 6-Cl | H |
| 3-79 | Me, Me | H, Me | 7-Cl | H |
| 3-80 | Me, Me | H, Me | 8-Cl | H |
| 3-81 | Me, Me | H, Me | 5-Me | H |
| 3-82 | Me, Me | H, Me | 6-Me | H |
| 3-83 | Me, Me | H, Me | 7-Me | H |
| 3-84 | Me, Me | H, Me | 8-Me | H |
| 3-85 | Me, Me | H, Me | 5-MeO | H |
| 3-86 | Me, Me | H, Me | 6-MeO | H |
| 3-87 | Me, Me | H, Me | 7-MeO | H |
| 3-88 | Me, Me | H, Me | 8-MeO | H |
| 3-89 | Me, Me | H, Me | 5,6-F₂ | H |
| 3-90 | Me, Me | H, Me | 6-F, 7-Me | H |
| 3-91 | Me, Me | Me, Me | H | H |

TABLE 3-continued (Ic)

| Compound No. | R1, R2 | R3, R4 | Xn | Ym |
|---|---|---|---|---|
| 3-92 | Me, Me | Me, Me | H | 5-F |
| 3-93 | Me, Me | Me, Me | H | 6-F |
| 3-94 | Me, Me | Me, Me | H | 7-F |
| 3-95 | Me, Me | Me, Me | H | 8-F |
| 3-96 | Me, Me | Me, Me | H | 2-Me |
| 3-97 | Me, Me | Me, Me | H | 4-Me |
| 3-98 | Me, Me | Me, Me | H | 8-Me |
| 3-99 | Me, Me | Me, Me | H | 8-MeO |
| 3-100 | Me, Me | Me, Me | 5-F | H |
| 3-101 | Me, Me | Me, Me | 5-F | 5-F |
| 3-102 | Me, Me | Me, Me | 5-F | 6-F |
| 3-103 | Me, Me | Me, Me | 5-F | 7-F |
| 3-104 | Me, Me | Me, Me | 5-F | 8-F |
| 3-105 | Me, Me | Me, Me | 5-F | 2-Me |
| 3-106 | Me, Me | Me, Me | 5-F | 4-Me |
| 3-107 | Me, Me | Me, Me | 5-F | 8-Me |
| 3-108 | Me, Me | Me, Me | 5-F | 8-MeO |
| 3-109 | Me, Me | Me, Me | 6-F | H |
| 3-110 | Me, Me | Me, Me | 7-F | H |
| 3-111 | Me, Me | Me, Me | 8-F | H |
| 3-112 | Me, Me | Me, Me | 5-Cl | H |
| 3-113 | Me, Me | Me, Me | 6-Cl | H |
| 3-114 | Me, Me | Me, Me | 7-Cl | H |
| 3-115 | Me, Me | Me, Me | 8-Cl | H |
| 3-116 | Me, Me | Me, Me | 5-Me | H |
| 3-117 | Me, Me | Me, Me | 6-Me | H |
| 3-118 | Me, Me | Me, Me | 7-Me | H |
| 3-119 | Me, Me | Me, Me | 8-Me | H |
| 3-120 | Me, Me | Me, Me | 5-MeO | H |
| 3-121 | Me, Me | Me, Me | 6-MeO | H |
| 3-122 | Me, Me | Me, Me | 7-MeO | H |
| 3-123 | Me, Me | Me, Me | 8-MeO | H |
| 3-124 | Me, Me | Me, Me | 5,6-F$_2$ | H |
| 3-125 | Me, Me | Me, Me | 6-F, 7-Me | H |
| 3-126 | Me, Me | cPen | H | H |
| 3-127 | cPen | Me, Me | H | H |
| 3-128 | Me. Me | cHex | H | H |
| 3-129 | cHex | Me, Me | H | H |
| 3-130 | Me, Et | H, H | 5-F | H |
| 3-131 | Me, Me | CH$_2$= | 5-F | H |
| 3-132 | Me, Me | H, F | 5-F | H |
| 3-133 | Me, Me | H, Cl | 5-F | H |
| 3-134 | Me, Me | F, F | H | H |
| 3-135 | Me, Me | F, F | 5-F | H |
| 3-136 | Me, Me | H, OH | 5-F | H |
| 3-137 | Me, Me | H, OMe | 5-F | H |
| 3-138 | Me, Me | O= | H | H |
| 3-139 | Me, Me | O= | 5-F | H |
| 3-140 | Me, Me | Me, OH | 5-F | H |
| 3-141 | Me, Me | Et, OH | 5-F | H |
| 3-142 | Me, Me | Me, OMe | 5-F | H |
| 3-143 | Me, Me | Me, OEt | 5-F | H |
| 3-144 | Me, Me | Et, OMe | 5-F | H |

A preferable compound among the aforementioned compounds is, a compound of Compound No. 1-32: 3-(5-fluoro-3,3-dimethyl-3,4-dihydroisoquinolin-1-yl)quinoline, a compound of Compound No. 1-44: 3-(5-chloro-3,3-dimethyl-3,4-dihydroisoquinolin-1-yl)quinoline, a compound of Compound No. 1-56: 3-(5-bromo-3,3-dimethyl-3,4-dihydroisoquinolin-1-yl)quinoline, a compound of Compound No. 1-117: 3-(5,6-difluoro-3,3-dimethyl-3,4-dihydroisoquinolin-1-yl)quinoline, a compound of Compound No. 1-185: 3-(5-fluoro-3-methyl-3-propyl -3,4-dihydroisoquinolin-1-yl)quinoline, a compound of Compound No. 1-387: 3-(3-methyl-3-trifluoromethyl-3,4-dihydroisoquinolin-1-yl)quinoline, a compound of Compound No. 1-425: 3-[3-methyl-3-(2,2,2-trifluoroethyl)-3,4-dihydroisoquinolin-1-yl]quinoline, a compound of Compound No. 1-502: 3-[3-methyl-3-(4-fluorophenyl)-3,4-dihydroisoquinolin-1-yl]quinoline, a compound of Compound No. 1-865: 3-(3,3,4,4-tetramethyl-3,4-dihydroisoquinolin-1-yl)quinoline, a compound of Compound No. 1-866: 3-(5-fluoro-3,3,4,4-tetramethyl-3,4-dihydroisoquinolin-1-yl)quinoline, a compound of Compound No. 1-918: 8-fluoro-3-(5-fluoro-3,3,4,4-tetramethyl-3,4-dihydroisoquinolin-1-yl) quinoline, a compound of Compound No. 1-919: 3-(5-fluoro-3,3,4,4-tetramethyl-3,4-dihydroisoquinolin-1-yl)-8-methylquinoline, a compound of Compound No. 1-929: 3-(4,4-difluoro-3,3-dimethyl-3,4-dihydroisoquinolin-1-yl)quinoline, a compound of Compound No. 1-930: 3-(4,4,5-trifluoro-3,3-dimethyl-3,4-dihydroisoquinolin-1-yl)quinoline, a compound of Compound No. 2-91: 3,3,4,4-tetramethyl-8b-quinolin-3-yl -4,8b-dihydro-3H-oxazireno[3,2-a]isoquino line, a compound of Compound No. 2-100: 5-fluoro-3,3,4,4-tetramethyl-8b-quinolin-3-yl-4,8b-dihydro-3H-oxazireno[3,2-a]isoquinoline, a compound of Compound No. 2-134: 4,4-difluoro-3,3-dimethyl-8b-quinolin-3-yl-4,8b-dihydro-3H-oxazireno[3,2-a]isoquinoline, a compound of Compound No. 2-135: 4,4,5-trifluoro-3,3-dimethyl-8b-quinolin-3-yl-4,8b-dihydro-3H-oxazireno[3,2-a]isoquinoline, a compound of Compound No. 3-100: 3-(5-fluoro-3,3,4,4-tetramethyl-2-oxido-3,4-dihydroisoquinolin-1-yl)quinoline, a compound of Compound No. 3-109: 3-(6-fluoro-3,3,4,4-tetramethyl-2-oxido-3,4-dihydroisoquinolin-1-yl)quinoline, a compound of Compound No. 3-134: 3-(4,4-difluoro-3,3-dimethyl-2-oxido-3,4-dihydroisoquinolin-1-yl)quinoline, or a compound of Compound No. 3-135: 3-(4,4,5-trifluoro-3,3-dimethyl-2-oxido-3,4-dihydroisoquinolin-1-yl)quinoline.

Compounds (Ia), (Ib) and (Ic) of the present invention are publicly known compounds, and are manufactured, for example, in accordance with methods disclosed in the pamphlet of International Publication WO 2005/070917 or method similar to them.

Compounds (Ia), (Ib) and (Ic) of the present invention are useful as a soil treating agent or a seed treating agent against various plant pathogens in agriculture and horticulture. For example, as the soil treating agent or as the seed treating agent, they show superior precautionary and/or preventive effects against diseases caused by various plant pathogens in agriculture and horticulture. They show superior preventive effects against various diseases, including for example rice blast, Bakanae disease of rice, Fusarium blight and seedling blight of wheat, Rhizoctonia seedling blight and Pythium damping-off of cucumber, Fusarium wilt of cucumber, damping-off or Fusarium wilt of tomato. Since the compounds of the present invention show superior preventive (precautionary) effects, they can prevent diseases by treatment before infection.

In the present invention, soil treatment means spraying on soil surface, injecting into soil, drenching into soil or mixing into soil, a composition comprising compounds of the present invention as an active ingredient. By treating soil by a composition comprising compounds of the present invention as an active ingredient, plants can be protected from pathogens of soil infection and aerial infection. Spraying on soil surface, drenching into soil and mixing into soil can be conducted from before or at sowing times throughout the growth of plants.

In the present invention, seed treatment means treating seeds by spraying a composition comprising compounds of the present invention as an active ingredient on plant seeds, treating seeds by coating a composition comprising compounds of the present invention as an active ingredient on plant seeds, treating seeds by dipping plant seeds into a composition comprising compounds of the present invention as an active ingredient or treating seeds by dust-coating a composition comprising compounds of the present invention as an active ingredient. By treating seeds with a composition comprising compounds of the present invention as an active ingredient, it is expected that preventive effects of seeds against pathogens adhered to seed surface and against pathogens that inherently infects inside seeds, and preventive effects of disease onsets against pathogen (soil pathogens etc.), onsets of which being observed after sowing, can be obtained.

An amount of applications and concentration of applications may vary depending on intended crops, intended diseases, degree of disease, drug forms of the compound, methods of applications and various environmental conditions. In a case where seeds are disinfected, an amount of compounds of the present invention used is usually 0.001 to 50 g per kg of seeds, preferably 0.01 to 10 g per kg. In a case of treating soil, an amount of compounds of the present invention used is usually 20 to 20,000 g per ha, preferably 100 to 10,000 g per ha. In a case where soil is treated by spraying on its surface, treated by injecting into it or treated by drenching into it, treating can be conducted using a composition comprising compounds of the present invention itself, or after diluting the composition to a desirable concentration. In a case where a composition comprising compounds of the present invention is made to come into contact with plant seeds, the plant seeds may be immersed into the agent as it is. In addition, a composition comprising compounds of the present invention may be used as itself or after it is diluted to a desirable concentration, by dipping into plant seeds, or dust-coating, spraying or coating plant seeds with the composition. In a case where seeds are treated by dust-coating, spraying or coating, an amount of the composition used (content of compounds of the present invention is 10 w/w % to 70 w/w %) is usually approximately 0.05 to approximately 50% per the weight of dry plant seeds, preferably 0.1 to 30%, and such amounts used are not limited within the range, and shall differ depending on forms of formulations and types of plant seeds as treatment subjects.

In the present invention, plant seeds mean those storing nutritions for embryo plants to germinate and used for agricultural propagations, including specifically seeds of corn, soybean, cotton, rice, sugar beet, wheat, barley, sunflower, tomato, cucumber, eggplant, spinach, split pea, pumpkin, sugarcane, tobacco, green pepper, coleseed, etc.; seed tuber of aroid, potato, sweet potato, Amorphophalus konjak, etc.; bulb of edible lily, tulip, etc.; or seed bulb of rakkyo, etc., and further include seeds and the like which have been subject to genetic transformation, including seeds of soybean, corn, cotton, etc., imparted with herbicide resistant properties; seeds of rice, tobacco, etc., adaptable in cold regions; or seeds of corn, cotton, potato, etc., with insecticidal substance-producing properties, which are plants that are generated by artificial operation of genes and the like and do not originally exist in nature. Here, the present invention is not limited to these.

When using compounds of the present invention, in a similar manner to the case of conventional agrichemical formulations, the compounds can be formulated into various kinds of formulations (compositions), including emulsions, dusts, wettable powders, solutions, granules, suspensions, in combination with adjuvants (including carriers). With respect to actual use of these formulations, they may be used as it is, or they may be diluted to a predetermined concentration by diluents such as water.

The adjuvant used may be a carrier, emulsifier, suspending agent, dispersing agent, spreading agent, penetrating agent, moistening agent, thickening agent, stabilizer and the like, and can be added as necessary.

The carrier used can be classified into a solid carrier and a liquid carrier. The solid carrier may be animal and plant powders such as starch, sugar, cellulose powder, cyclodextrin, activated charcoal, soybean powder, wheat flour, chaff, wood flour, fish flour and powdered milk; or mineral powders such as talc, kaolin, bentonite, organic bentonite, calcium carbonate, calcium sulfate, sodium bicarbonate, zeolite, diatomaceous earth, white carbon, clay, alumina, silica and sulfur powder. The liquid carrier may be water; animal and plant oils such as soybean oil, cotton oil and corn oil; alcohols such as ethyl alcohol and ethylene glycol; ketones such as acetone and methyl ethyl ketone; ethers such as dioxane and tetrahydrofuran; aliphatic/aromatic hydrocarbons such as kerosene, lamp oil, liquid paraffin, xylene, trimethylbenzene, tetramethylbenzene, cyclohexane, solvent naphtha; halogenated hydrocarbons such as chloroform and chlorobenzene; acid amides such as dimethylformamide; esters such as ethyl acetate and glycerin esters of fatty acids; nitriles such as acetonitrile; sulfur containing compounds such as dimethylsulfoxide; or N-methylpyrrolidone.

Weight ratio with respect to the formulation of the compound of the present invention and the adjuvant is usually 0.05:99.95 to 90:10, preferably 0.2:99.8 to 80:20.

The compound of the present invention can be used in combination with or together with other agrochemicals such as fungicides and antivirus agents as necessary.

The fungicides used may be, for example, pyrimidinamine compounds such as 2-anilino-4-methyl-6-(1-propynyl)pyrimidine (common name: mepaniprim) and 4,6-dimethyl-N-phenyl-2-pyrimidinamine (common name: pyrimethanil); azole compounds such as 1-(4-chlorophenoxy)-3,3-dimethyl-1-(1H-1,2,4-triazol -1-yl)butanone (common name: triadimefon), 1-(biphenyl-4-yloxy)-3,3-dimethyl-1-(1H,1,2,4-triazol-1-yl)butan-2-ol (common name: bitertanol), 1-{N-(4-chloro-2-trifluoromethylphenyl)-2-propoxy-acetoimidoyl}imidazole (common name: triflumizole), 1-{2-(2,4-dichlorophenyl)-4-ethyl-1,3-dioxolan-2-ylmethyl}-1H-1,2,4-triazole (common name: etaconazole), 1-{2-(2,4-dichlorophenyl)-4-propyl-1,3-dioxolan-2-ylmethyl}-1H-1, 2,4-triazole (common name: propiconazole), 1-{2-(2,4-dichlorophenyl)pentyl}-1H-1,2,4-triazole (common name: penconazole), bis(4-fluorophenyl)(methyl)(1H-1,2,4-triazol-1-ylmethyl)silane (common name: flusilazole), 2-(4-chlorophenyl)-2-(1H-1,2,4-triazol -1-ylmethyl)-hexanenitrile (common name: myclobutanil), (2RS,3RS)-2-(4-chlorophenyl)-3-cyclopropyl-1-(1H-1,2,4-triazol-1-yl) butan-2-ol (common name: cyproconazole), (RS)-1-(4-chlorophenyl)-4,4-dimethyl-3-(1H-1,2,4-triazol 1-1-ylmethyl)pentan-3-ol (common name: terbuconazole), (RS)-

2-(2,4-dichlorophenyl)-1-(1H-1,2,4-triazol-1-yl)hexan-2-ol (common name: hexaconazole), (2RS,5RS)-5-(2,4-dichlorophenyl)tetrahydro -5-(1H-1,2,4-triazol-1-ylmethyl)-2-furyl 2,2,2-trifluoroethylether (common name: furconazolecis), N-propyl-N-{2-(2,4,6-trichlorophenoxy)ethyl}imidazol-1-carboxamide (common name: prochloraz) and 2-(4-fluorophenyl)-1-(1H-1,2,4-triazol-1-yl)-3-trimethylsilylpropan-2-ol (common name: simeconazole); quinoxaline compounds such as 6-methyl-1,3-dithiolo[4,5-b]quinoxalin-2-one (common name: chinomethionate); dithiocarbamate compounds such as polymer of manganese ethylenebis(dithiocarbamate) (common name: maneb), polymer of zinc ethylenebis(dithiocarbamate) (common name: zineb), coordination product of zinc (Zn) and manganese ethylenebis(dithiocarbamate)(maneb) (common name: manzeb), dizinc bis(dimethyldithiocarbamate)ethylenebis(dithiocarbamate) (common name: polycarbamate) and polymer of zinc propylenebis(dithiocarbamate) (common name: probineb); organic chlorine compounds such as 4,5,6,7-tetrachlorophthalide (common name: fthalide), tetrachloroisophthalonitrile (common name: chlorothalonil) and pentachloronitrobenzene (common name: quintozene); benzimidazole compounds such as methyl 1-(butylcarbamoyl)benzimidazol-2-yl carbamate (common name: benomyl), dimethyl 4,4'-(o-phenylene)bis(3-thioalophanate) (common name: thiphanatemethyl) and methylbenzimidazol-2-yl carbamate (common name: carbendazim); pyridinamine compounds such as 3-chloro-N-(3-chloro-2,6-dinitro-4-α,α,α-trifluorotolyl)-5-trifluoromethyl-2-pyridinamine (common name: fluazinam); cyanoacetamide compounds such as 1-(2-cyano-2-methoxy-iminoacetyl)-3-ethyl urea (common name: cymoxanil); phenyl amide compounds such as methyl N-(2-methoxyacetyl)-N-(2,6-xylyl)-DL-alaninate (common name: metalaxyl), 2-methoxy-N-(2-oxo-1,3-oxazolidin-3-yl)aceto-2',6'-xylidide (common name: oxadixyl), (±)-α-2-chloro-N-(2,6-xylyl)acetamide)-γ-butyrolactone (common name: ofurace), methyl N-phenylacetyl-N-(2,6-xylyl)-DL-alaninate (common name: benalaxyl), methyl N-(2-furoyl)-N-(2,6-xylyl)-DL-alaninate (common name: furalaxyl) and (±)-α-[N-(3-chlorophenyl)cyclopropanecarboxamide]-γ-butyrolactone (common name: cyprofuram); sulfenic acid compounds such as N-dichlorofluoromethylthio-N',N'-dimethyl-N-phenyl sulfamide (common name: dichlofluanid); copper compounds such as cupric hydroxide (common name: cupric hydroxide) and copper 8-quinolate (common name: oxine copper); isoxazole compounds such as 5-methylisoxazole-3-ol (common name: hydroxyisoxazole); organic phosphorus compounds such as aluminum tris(ethylphosphonate) (common name: fosetyl aluminum), O-2,6-dichloro-p-tolyl-O,O-dimethylphosphorothioate (common name: tolclofos-methyl), S-benzyl O,O-diisopropylphosphorothioate, O-ethyl S,S-diphenylphosphorodithioate and aluminum ethyl hydrogen phosphonate; N-halogenothioalkyl compounds such as N-(trichloromethylthio)cyclohexy-4-ene-1,2-dicarboximide (common name: captan), N-(1,1,2,2-tetrachloroethylthio)cyclohexy-4-ene-1,2-dicarboximide (common name: captafol) and N-(trichloromethylthio)phthalimide (common name: folpet); dicarboximide compounds such as N-(3,5-dichlorophenyl)-1,2-dimethylcyclopropan-1,2-dicarboximide (common name: procymidone), 3-(3,5-dichlorophenyl)-N-isopropopyl-2,4-dioxoimidazolidine-1-carboxamide (common name: iprodione) and (RS)-3-(3,5-dichlorophenyl)-5-methyl-5-vinyl-1,3-oxazolidine-2,4-dione (common name: vinclozolin); benzanilide compounds such as α,α,α-trifluoro-3'-isopropoxy-o-toluanilide (common name: flutolanil) and 3'-isopropoxy-o-toluanilide (common name: mepronil); piperazine compounds such as N,N'-[piperazin-1, 4-diylbis{(trichloromethyl)methylene}]diformamide (common name: triforine); pyridine compounds such as 2',4'-dichloro-2-(3-pyridyl)acetophenone O-methyloxime (common name: pyrifenox); carbinol compounds such as (±)-2,4'-dichloro-α-(pyrimidin-5-yl)benzhydryl alcohol (common name: fenarimol) and (±)-2,4'-difluoro-α-(1H-1,2,4-triazol-1-ylmethyl)benzhydryl alcohol (common name: flutriafol); piperidine compounds such as (RS)-1-{3-(4-t-butylphenyl)-2-methylpropyl}piperidine (common name: fenpropidine); morpholine compounds such as (±)-cis-4-{3-(4-t-butylphenyl)-2-methylpropyl}-2,6-dimethylmorpholine (common name: fenpropimorph); organic tin compounds such as triphenyltin hydroxide (common name: fentin hydroxide) and triphenyltin acetate (common name: fentin acetate); urea compounds such as 1-(4-chlorobenzyl)-1-cyclopentyl-3-phenylurea (common name: pencycuron); cinnamic acid compounds such as (E,Z)4-{3-(4-chlorophenyl)-3-(3,4-dimethoxyphenyl)acryloyl}morpholine (common name: dimethomorph); phenylcarbamate compounds such as isopropyl 3,4-diethoxycarbanilate (common name: diethofencarb); or cyanopyrrole compounds such as 3-cyano-4-(2,2-difluoro-1,3-benzodioxol-4-yl)pyrrole (common name: fludioxonil) and 3-(2',3'-dichlorophenyl)-4-cyano-pyrrole (common name: fenpiclonil); and antivirus agent used may be a BT agent or an insect disease virus agent.

EXAMPLES

The present invention will be described in detail with reference to the following Examples, but the present invention is not limited to these.

Here, each of the compounds of Compound Nos. 1-32, 1-44, 1-56, 1-117, 1-185, 1-387, 1-425, 1-502, 1-865, 1-866, 1-918, 1-919, 1-929, 1-930, 2-91, 2-100, 2-134, 2-135, 3-100, 3-109, 3-134 and 3-135 used in the Examples are, respectively, described as Examples 2, 18, 22, 52, 58, 68, 69, 72, 122, 114, 164, 165, 177, 178, 196, 193, 237, 203, 204, 209, 218 and 219 of International Publication WO 2005/070917.

Example 1

Treatment Test at Sowing Time or Transplanting Time (Rice Blast)

The soil in a nursery box of test plants (rice: Sachikaze) was each treated at sowing time or transplanting time with the solution of wettable powders containing the compound of the present invention dissolved in water so as the application rate to be 400 g a.i./10 a. The test plants were cultivated for one week. A suspension of rice blast spores was inoculated by spraying the suspension to the test plants cultivated by using the above method. The pots were placed in an inoculation room, room temperature of which being 20-23° C., and infection of the disease was promoted. Severity of the disease was observed 7 days after inoculation. Tests were carried out in duplicate.

Here, the disease severity of the test plants was observed by the naked eyes, judged in accordance with the following criteria and expressed (in 4 levels of 0 to 3 in which the disease severity of the untreated plants was 3).
Disease Severity:
  0 (No lesion of the disease)
  1 (Lesion of the disease less than 40% of the untreated area)
  2 (Lesion of the disease 40% or more to less than 80%)
  3 (Lesion of the disease 80% or more)
According to the results of the tests, the disease severity was 0, when compounds of Compound Nos. 1-32, 1-44, 1-56, 1-117, 1-185, 1-387, 1-425, 1-502, 1-866, 1-918, 1-919, 1-929, 1-930, 2-91, 3-100, 3-109, 3-134 or 3-135 was used.

Example 2

Soil Disease Prevention Test (Cucumber Fusarium Wilt)

Seeds of pot-cultivated test plants (Sagamihanpaku) were sown to an inoculated soil which was adjusted so that cucumber Fusarium wilt spores were $1\times10^5$ per 1 g of soil. At the time of sowing, the solution of wettable powders containing the compound of the present invention dissolved in water was drenched into the soil at the rate of 10,000 g/ha. The disease severity was observed 3 weeks after treatment. Tests were carried out in duplicate.

Here, the disease severity of the test plants was observed by the naked eyes, judged in accordance with the following criteria, and expressed (in 4 levels of 0 to 3 in which the disease severity of the untreated plants was 3).

Disease Severity:
  0 (No symptom)
  1 (Yellowing)
  2 (Wilting)
  3 (Death)

According to the results of the tests, the disease severity of was 0, when compounds of Compound Nos. 1-866, 1-918, 1-919, 1-929, 1-930, 2-100, 2-135, 3-100 or 3-135 was used.

Example 3

Seed Disinfection Test (Rice Blast, Rice "Bakanae" Disease)

20 g of moistened seeds of test plants (Sachikaze or Tanginbouzu: seeds inoculated with rice blast or rice "Bakanae" disease) were coated with wettable powders containing the compound of the present invention so as the application rate to be 0.02% a.i., added with 20 ml of distilled water and incubated for 1 day at 25° C. The test plants treated by the above method were cultivated in pots for 3 weeks, and the disease severity was observed. Tests were carried out in duplicate. Disease prevention effect was judged in accordance with the following criteria.

Regarding the seeds infected with rice blast, numbers of lesion with respect to the germination rate were observed, and the infection rate was calculated. Prevention value was calculated by taking the infection rate of untreated plants as 100.

According to the results of the test, the prevention value was 80 or more, when compounds of Compound Nos. 1-32, 1-866, 1-929, 1-930, 2-100, 2-134, 2-135, 3-100, 3-134 or 3-135 was used.

Regarding the seeds infected with rice "Bakanae" disease, numbers of the diseased seedling and germination rate were observed, and infection rate was calculated. Prevention value was calculated by taking the infection rate of untreated plants as 100.

According to the results of the test, the prevention value was 80 or more, when compounds of Compound Nos. 1-32, 1-865, 1-866, 1-929, 1-930, 2-100, 2-139, 3-100, 3-134 or 3-135 was used.

Example 4

Seed Treatment Test (Wheat Fusarium Seedling Blight)

20 g of moistened seeds (seeds inoculated with wheat Fusarium blight) of test plants (Nourin 61 gou) were coated with wettable powder containing the compound of the present invention so as the application rate to be 0.1% a.i. The seeds (30 grains) treated by the above method were sown, and the disease severity was observed after 2 weeks. Tests were carried out in duplicate.

Here, the disease severity of the test plants was observed by the naked eyes and evaluated in accordance with the following criteria, and expressed (in 4 levels of 0 to 3 in which the disease severity of the untreated plants was 3).

Disease Severity:
  0: No symptom.
  1: Yellowing.
  2: Wilting.
  3: Blighted.

According to the results of the tests, the disease severity was 0, when compounds of Compound Nos. 1-866, 1-918, 1-919, 1-929, 1-930, 2-100, 2-135, 3-100 or 3-135 was used.

Example 5

Seed Treatment Test (Cucumber Fusarium Wilt)

10 g of moistened seeds (seeds inoculated with cucumber Fusarium wilt) of test plants (Sagamihanpaku) were coated with wettable powders containing the compound of the present invention so as the application rate to be 0.1% a.i. The seeds (10 grains) treated by the above method were sown and the disease severity was observed after 3 weeks. Tests were carried out in duplicate.

Here, the disease severity of the test plants was observed by the naked eyes and evaluated in accordance with the following criteria, and expressed (in 4 levels of 0 to 3 in which the disease severity of the untreated plants was 3).

Disease Severity:
  0: No symptom.
  1: Yellowing.
  2: Wilting.
  3: Death.

According to the results of the tests, the disease severity was 0, when compounds of Compound Nos. 1-866, 1-918, 1-919, 1-929, 1-930, 2-100, 2-135, 3-100 or 3-135 was used.

Example 6

Seed Treatment Test (Cucumber Fusarium Wilt)

10 g of moistened seeds of test plants (cultivar of cucumber: Sagamihanpaku) were coated with wettable powders containing the compound of the present invention so as the application rate to be 0.1% a.i. The seeds (10 grains) treated by the above method were sown in the soil inoculated with cucumber Fusarium wilt ($1\times10^5$ spores), and the disease severity was observed after 3 weeks. Tests were carried out in duplicate.

Here, the disease severity of the test plants was observed by the naked eyes and evaluated in accordance with the following criteria, and expressed (in 4 levels of 0 to 3 in which the disease severity of the untreated plants was 3).

Disease Severity:
  0: No symptom.
  1: Yellowing.
  2: Wilting.
  3: Death.

According to the results of the tests, the disease severity was 0, when compounds of Compound Nos. 1-866, 1-918, 1-919, 1-929, 1-930, 2-100, 2-135, 3-100 or 3-135 was used.

Example 7

Seed Treatment Test (Cucumber Damping-Off)

10 g of moistened seeds of test plants (Sagamihanpaku) are coated with wettable powders containing the compound of the present invention so as the application rate to be 0.1% a.i. The seeds (10 grains) treated by the above method are sown in the soil inoculated with cucumber damping-off fungi (*Pythium aphanidermatum, Pythium megalocantham*), and the disease severity is observed after 2 weeks. Tests are carried out in duplicate.

Example 8

Seed Treatment Test 2 (Cucumber Damping-Off)

10 g of moistened seeds of test plants (Sagamihanpaku) are coated with wettable powders containing the compound of the present invention so as the application rate to be 0.1% a.i. The seeds (10 grains) treated by the above method are sown in the soil inoculated with cucumber damping-off fungi (*Rhizoctonia solani*), and the disease severity is observed after 2 weeks. Tests are carried out in duplicate.

Industrial Applicability

Compounds of the present invention can be used as a soil treating agent or as a seed treating agent, and are superior as the soil treating agent or as the seed treating agent, since they show outstanding effects against various plant pathogens, particularly against rice blast without causing damages to the host plants.

Plant diseases against which compounds of the present invention demonstrate excellent effects are for example rice blast, Bakanae disease of rice, Fusarium blight and seedling blight of wheat, Rhizoctonia seedling blight and Pythium damping-off of cucumber, Fusarium wilt of cucumber, damping-off or Fusarium wilt of tomato, but fungal spectrum of compounds of the present invention is not limited to these.

The invention claimed is:

1. A method for treating or controlling a plant disease selected from the group consisting of rice blast, Bakanae disease of rice, *Fusarium* blight of wheat, seedling blight of wheat, *Rhizoctonia* seedling blight of cucumber, *Pythium* damping-off of cucumber, *Fusarium* wilt of cucumber, damping off of tomato and *Fusarium* wilt of tomato comprising treating plant seeds with a seed treating composition comprising one or more compounds selected from the group consisting of
    3-(5-fluoro-3,3,4,4-tetramethyl-3,4-dihydroisoguinolin-1-yl)quinoline,
    8-fluoro-3-(5-fluoro-3,3,4,4-tetramethyl-3,4-dihydroisoquinolin-1-yl)quinoline,
    3-(5-fluoro-3,3,4,4-tetramethyl-3,4-dihydroisoquinolin-1-yl)-8-methylquinoline,
    3-(4,4-difluoro-3,3-dimethyl-3,4-dihydroisoquinolin-1-yl)quinoline,
    3-(4,4,5-trifluoro-3,3-dimethyl-3,4-dihydroisoquinolin-1-yl)quinoline,
    5-fluoro-3,3,4,4-tetramethyl-8b-quinolin-3-yl-4,8b-dihydro-3H-oxazireno[3,2-a]isoquinoline,
    4,4,5-trifluoro-3,3-dimethyl-8b-quinolin-3-yl-4,8b-dihydro-3H-oxazireno[3,2-a]isoquinoline,
    3-(5-fluoro-3,3,4,4-tetramethyl-2-oxido-3,4-dihydroisoquinolin-1-yl)quinoline, and
    3-(4,4,5-trifluoro-3,3-dimethyl-2-oxido-3,4-dihydroisoquinolin-1-yl)quinoline, as an active ingredient,
    wherein the treatment of the plant seeds is carried out by spraying the composition on the plant seeds, coating the plant seeds with the composition, dipping the plant seeds into the composition or dust-coating the plant seeds with the composition, to control pathogens which adhere to the surface of plant seeds and to control pathogens which infect the inside of the plant seeds, or to control an onset of said disease caused by a pathogen or an onset of said disease which is observed after the sowing of the plant seeds.

2. The method according to claim 1, wherein the compounds are applied in an amount of 0.001 to 50 g per kg of the plant seeds in a case where the plant seeds are disinfected.

3. The method according to claim 1, wherein the compounds are applied in an amount of 0.01 to 10 g per kg of the plant seeds in a case where the plant seeds are disinfected.

4. The method according to claim 1, wherein the compound is selected from the group consisting of
    3-(5-fluoro-3,3,4,4-tetramethyl-3,4-dihydroisoquinolin-1-yl)quinoline,
    3-(4,4-difluoro-3,3-dimethyl-3,4-dihydroisoquinolin-1-yl)quinoline,
    3-(4,4,5-trifluoro-3,3-dimethyl-3,4-dihydroisoquinolin-1-yl)quinoline,
    3-(5-fluoro-3,3,4,4-tetramethyl-2-oxido-3,4-dihydroisoquinolin-1-yl)quinoline,
    5-fluoro-3,3,4,4-tetramethyl-8b-quinolin-3-yl-4,8b-dihydro-3H-oxazireno[3,2-a]isoquinoline and
    3-(4,4,5-trifluoro-3,3-dimethyl-2-oxido-3,4-dihydroisoquinolin-1-yl)quinoline.

5. The method according to claim 1, wherein the compound is 3-(5-fluoro-3,3,4,4-tetramethyl-3,4-dihydroisoquinolin-1-yl)quinoline.

6. The method according to claim 1, wherein the compound is 5-fluoro-3,3,4,4-tetramethyl-8b-quinolin-3-yl-4,8b-dihydro-3H-oxazireno[3,2-a]isoquinoline.

7. The method according to claim 1, wherein the compound is 3-(5-fluoro-3,3,4,4-tetramethyl-2-oxido-3,4-dihydroisoquinolin-1-yl)quinoline.

* * * * *